United States Patent
Takahori

(10) Patent No.: US 12,171,413 B2
(45) Date of Patent: Dec. 24, 2024

(54) SPERM COLLECTION DEVICE

(71) Applicant: TENGA Co., Ltd., Tokyo (JP)

(72) Inventor: Kyohei Takahori, Tokyo (JP)

(73) Assignee: TENGA Co., Ltd., Tokyo (JP)

( * ) Notice: Subject to any disclaimer, the term of this patent is extended or adjusted under 35 U.S.C. 154(b) by 835 days.

(21) Appl. No.: 17/315,025

(22) Filed: May 7, 2021

(65) Prior Publication Data

US 2021/0353269 A1 Nov. 18, 2021

(30) Foreign Application Priority Data

May 12, 2020 (JP) .................................. 2020-83916

(51) Int. Cl.
*A61B 10/00* (2006.01)
*A61F 5/453* (2006.01)
*A61H 19/00* (2006.01)

(52) U.S. Cl.
CPC .......... *A61B 10/0058* (2013.01); *A61F 5/453* (2013.01); *A61H 19/32* (2013.01); *A61H 2201/1602* (2013.01)

(58) Field of Classification Search
CPC ......... A61H 19/00; A61H 19/32; A61F 5/453; A61B 10/0058
USPC .......................................................... 600/38
See application file for complete search history.

(56) References Cited

U.S. PATENT DOCUMENTS

| 7,753,895 B2 | 7/2010 | Matsuura |
| 9,615,693 B1 * | 4/2017 | Merritt ................ A47J 37/0704 |
| 2015/0164678 A1 | 6/2015 | Lee et al. |
| 2016/0143354 A1 * | 5/2016 | Liu ........................ A24F 40/60 |
|  |  | 131/329 |
| 2016/0317380 A1 | 11/2016 | Gutierrez |
| 2018/0021212 A1 | 1/2018 | Matsuura |

FOREIGN PATENT DOCUMENTS

| CN | 101247763 B | 1/2011 |
| JP | 2016-504122 A | 2/2016 |
| WO | WO2015/092081 A1 | 6/2015 |
| WO | WO2016/132462 A1 | 8/2016 |

OTHER PUBLICATIONS

Taiwan Intellectual Property Office, Office Action dated Mar. 4, 2024 in Taiwanese Patent Application No. 110107646, 8 pages.

* cited by examiner

*Primary Examiner* — Samuel G Gilbert
(74) *Attorney, Agent, or Firm* — MASUVALLEY & PARTNERS; Peter Martinez

(57) ABSTRACT

The sperm collection device includes a core member having an insertion hole for a penis and an insertion space, and a container having an internal space in which the core member is accommodated. The container includes a cylindrical base unit having a base end open in an axial direction of the base unit and attached to an insertion-hole-side end of the core member, and a cylindrical movable unit having a base end open in an axial direction of the movable unit and a front end being closed, and attached rotatably around an axis of the movable unit with respect to the other end of the base unit. In an overlapping part in which the base end of the movable unit overlaps the other end of the base unit, an airflow path and an adjustment mechanism are provided.

7 Claims, 17 Drawing Sheets

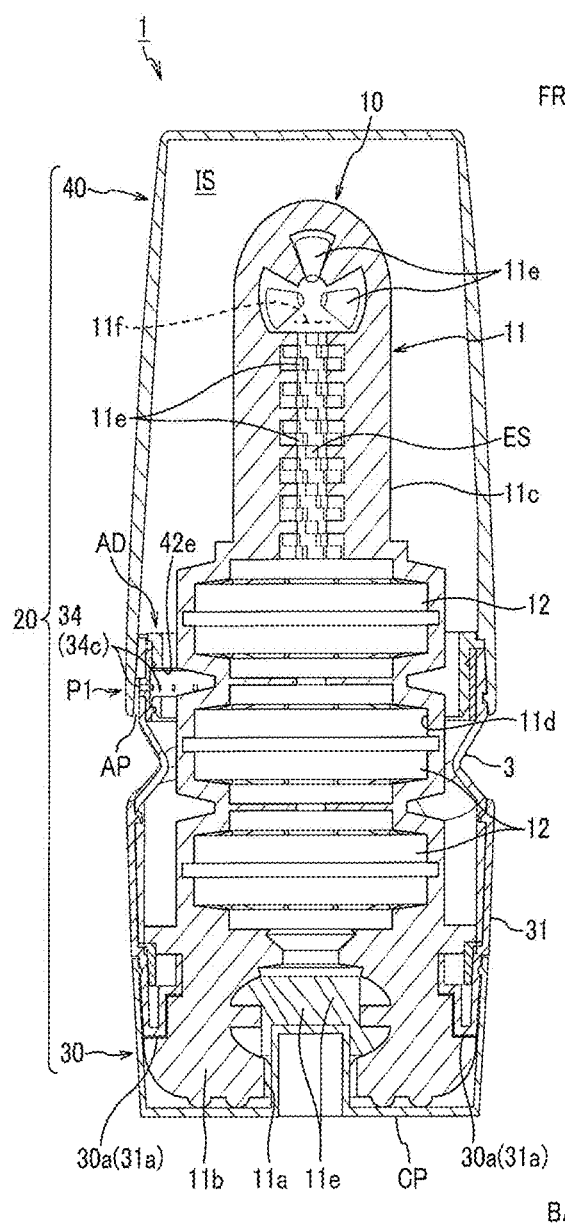
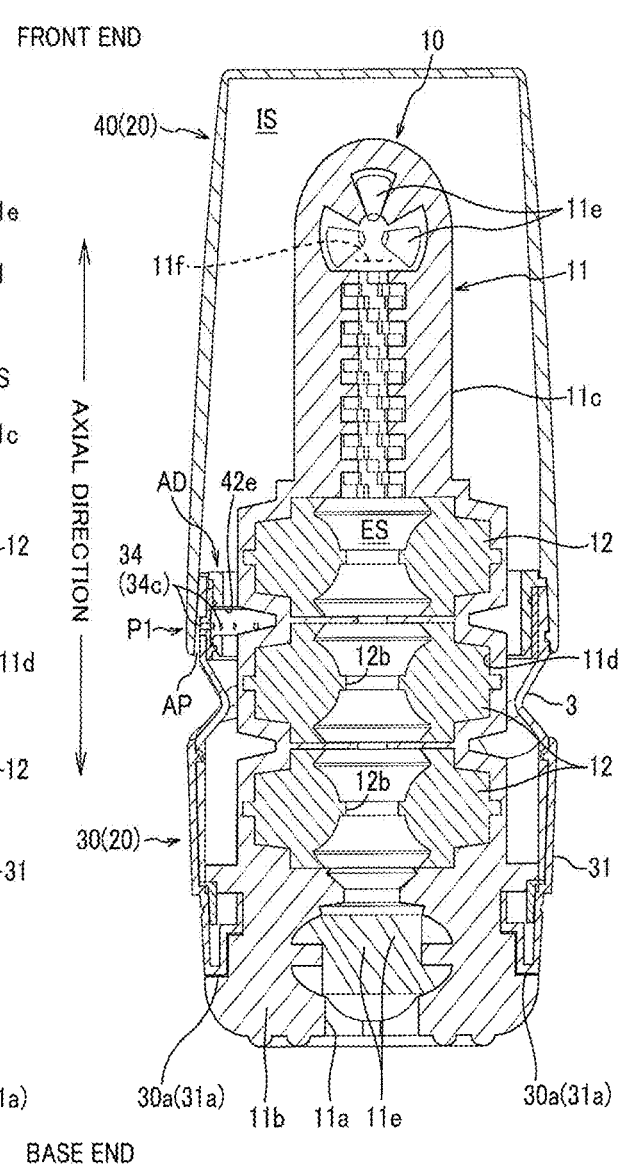

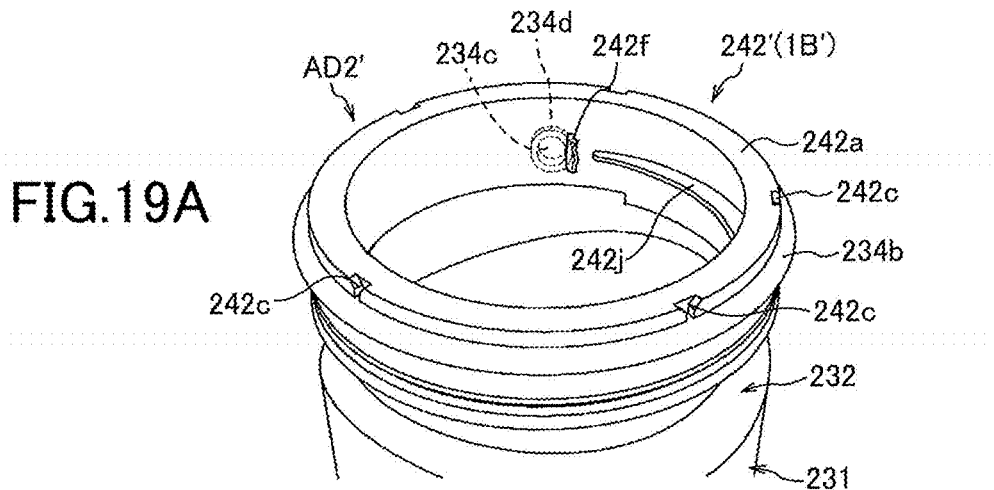
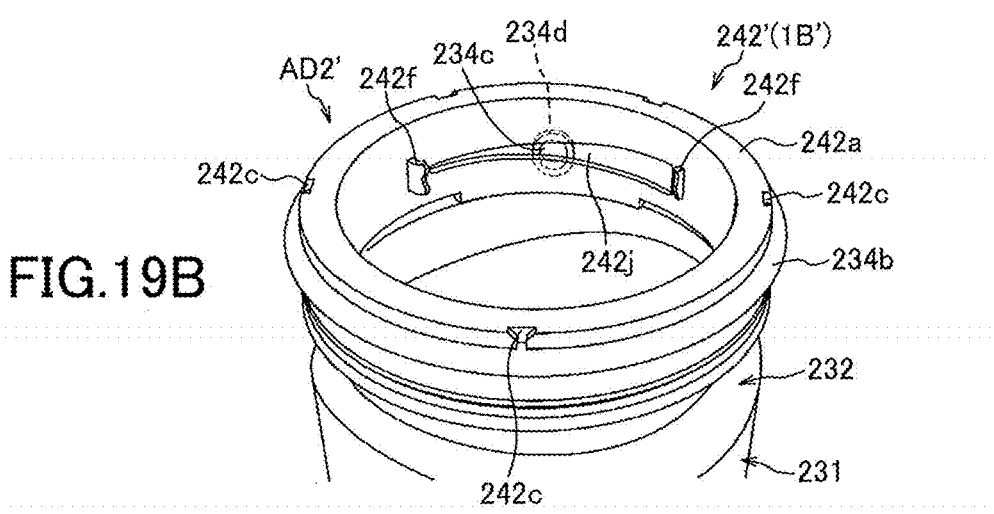
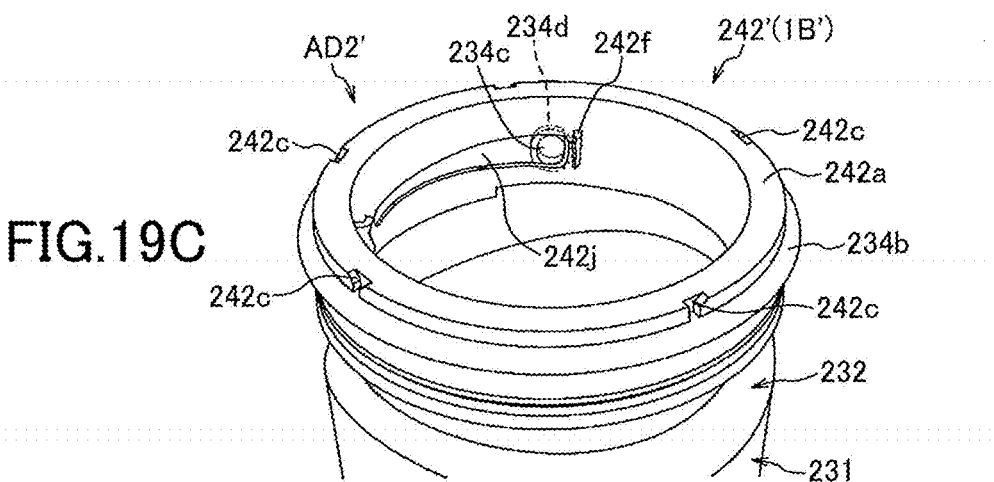

SPERM COLLECTION DEVICE

CROSS-REFERENCE TO RELATED APPLICATION

This application is based upon and claims the benefit of priority of the prior Japanese Patent Application No. 2020-083916, filed on May 12, 2020, the entire contents of which are incorporated herein by reference.

FIELD

The present invention relates to a sperm collection device and more particularly to improvement of conventional sperm collection devices used according to the demands for medical studies and treatment and the social demands for prevention of sex crimes, prevention of prostitution, and prevention of spreading of sexually transmitted diseases.

BACKGROUND

Various sperm collection devices (ejaculation facilitating devices for facilitating ejaculation) for collecting sperms have been proposed for medical studies and treatment.

A sperm collection device is used according to the medical demands such as examining the sexual function of a husband based on collected sperms in order to find out the cause of infertility between the husband and a wife, treating sexual dysfunctions, and obtaining and storing sperms for artificial insemination. Further, the sperm collecting device is used to satisfy various social needs such as prevention of sex crimes, prevention of prostitution, and reduction in the number of people infected with sexually transmitted diseases by solving personal sexual desire.

The sperm collection device is means that has an insertion space in which a penis is inserted, gives stimulations to a top end portion of the penis by frictions caused by inward and outward movements of the penis in the insertion space, and facilitates ejaculation.

For example, International Publication No. WO2016/132462 discloses an ejaculation facilitating device that includes a cylindrical container made of a rigid plastic material and having a base end open in a longitudinal direction of the cylindrical container and a front end with an air hole, and a core member made of gel resin, accommodated in the container, and having an insertion space extending toward an inner side of the core member from an insertion hole of a base end in a longitudinal direction of the core member.

The ejaculation facilitating device described in International Publication No. WO2016/132462 gives stimulations to a top end portion of a penis and facilitates ejaculation when the penis inserted from the insertion hole moves inwardly and outwardly in the insertion space. Further, a decompressing device attached on a front-end side of the container decompresses the container through the air hole, thereby giving strong stimulations to the penis.

International Publication No. WO2015/092081 discloses a unisex masturbation device that includes an internal body made of elastic resin and having an insertion hole for a penis at a base end in a longitudinal direction of the internal body and an insertion space continuous to the insertion hole and present in the internal body, a bottle-shaped container that has a base end open in a longitudinal direction of the container and a front end being closed and accommodates the internal body, and an air amount adjustment ring rotatable with respect to an outer circumferential surface of the container that is present near the base end of the container. The masturbation device described in International Publication No. WO2015/092081 is configured to give stimulations to a top end portion of a penis when the penis inserted from the insertion hole moves inwardly and outwardly in the insertion space.

Further, the masturbation device described in International Publication No. WO2015/092081 has a container-side opening on a side surface present near the base end of the container in the longitudinal direction, and a ring-side opening in the air amount adjustment ring. The masturbation device changes, based on a rotational amount of the air amount adjustment ring, the area of an overlapping part in which the container-side opening overlaps the ring-side opening. The masturbation device adjusts, based on the area of the overlapping part of the openings, the flow rate of air flowing in and out of the container, and adjusts the strength of stimulations to be given to a penis.

In the masturbation device described in International Publication No. WO2015/092081, the container-side opening and the ring-side opening are provided on the outer circumferential surface of the container. Therefore, a user may unintentionally close the ring-side opening with his fingers when using the masturbation device. When the ring-side opening on the outer circumferential surface of the container is closed by fingers, air hardly flows in and out of the container, and inconvenience may occur, such as reduction of the effect of facilitating ejaculation due to a change in stimulations that is not intended by a user.

The present invention has been achieved in view of the above problems, and an object of the present invention is to prevent a change in stimulations that is not intended by a user when a sperm collection device is used.

SUMMARY OF THE INVENTION

In order to solve the above problems, the present invention provides a sperm collection device, the sperm collection device comprising: a core member that is made of an elastic material and has an insertion hole for a penis and an insertion space in which the penis inserted in the insertion hole relatively moves inwardly and outwardly; and a container having an internal space in which the core member is accommodated, wherein the container includes a cylindrical base unit that has one end open in an axial direction of the base unit and attached to an insertion-hole-side end of the core member and the other end open in the axial direction, and a cylindrical movable unit that has one end open in an axial direction of the movable unit and the other end being closed and is attached rotatably around an axis of the movable unit with respect to the other end of the base unit, the one end of the movable unit overlaps the other end of the base unit, and an airflow path is provided in an overlapping part in which the one end of the movable unit overlaps the other end of the base unit, and an adjustment mechanism that adjusts, based on a rotational angle of the movable unit with respect to the base unit, a flow rate of air flowing in and out of the container is provided in the overlapping part.

According to the present invention, it is possible to prevent a change in stimulations that is not intended by a user when a sperm collection device is used.

BRIEF DESCRIPTION OF DRAWINGS

FIG. 1A is a vertical sectional view of a sperm collection device, and FIG. 1B is a vertical sectional view for explaining an insertion space within a core member;

FIG. 19A is an explanatory diagram of a state in which a movable-cylinder-side opening does not overlap the packing-side opening, FIG. 19B is an explanatory diagram of a state in which the flow rate of air is adjusted to an intermediate level, and FIG. 19C is an explanatory diagram of a state in which the flow rate of air is adjusted to the maximum level.

DESCRIPTION OF EMBODIMENTS

Outline and Characteristics of Sperm Collection Device 1

Embodiments of the present invention will be explained below with reference to the accompanying drawings.

Figure 2:
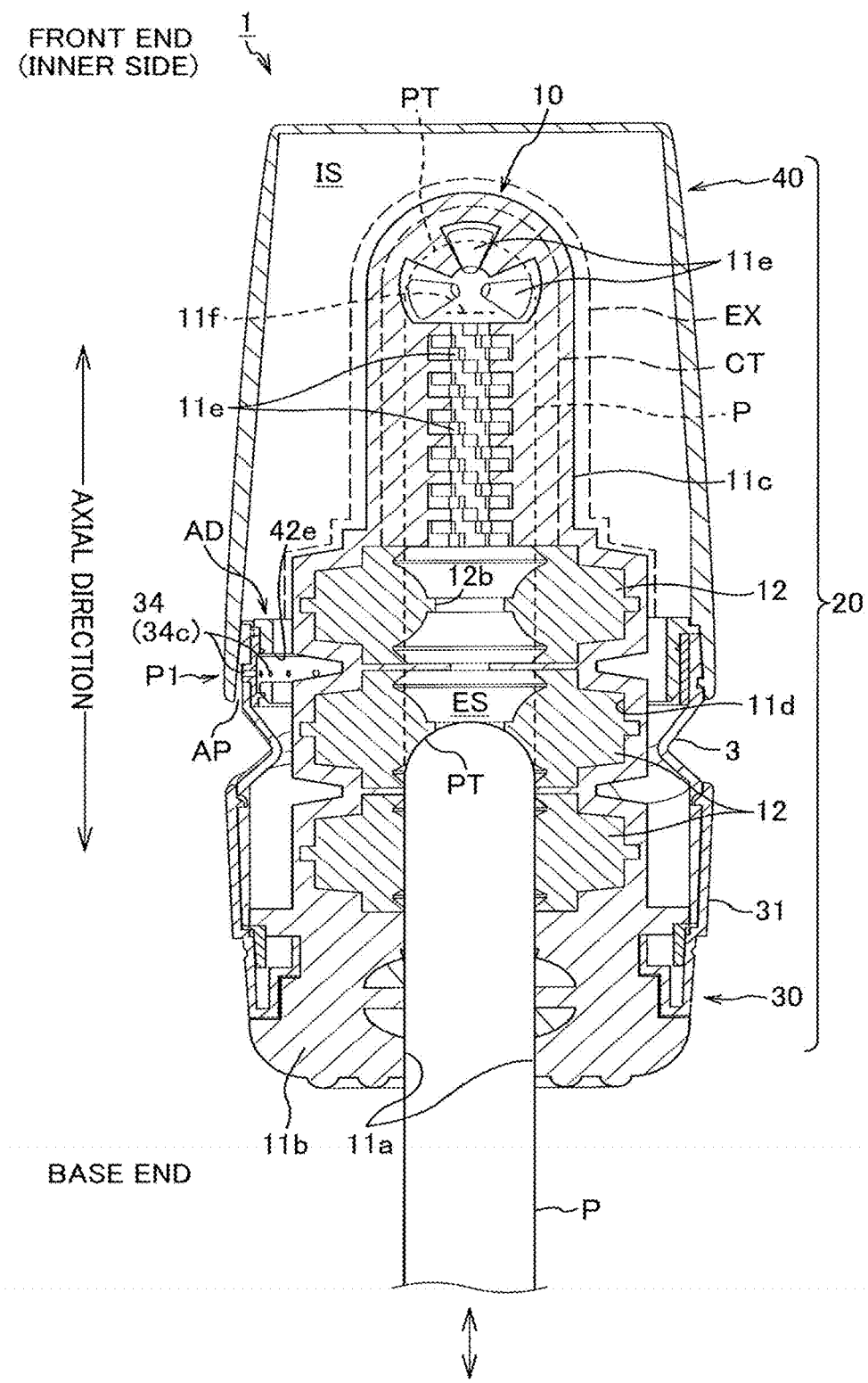
FIG. 2 is an explanatory diagram of a usage state of the sperm collection device.

First, an outline and characteristics of a sperm collection device 1 are described. FIG. 1A is a sectional view of the sperm collection device 1, FIG. 1B is a sectional view for explaining an insertion space ES within a core member 10, and FIG. 2 is an explanatory diagram of a usage state of the sperm collection device 1.

The sperm collection device 1 illustrated in FIGS. 1A and 1B includes the core member 10 that is made of a cylindrical elastic material and has the insertion space ES in which a penis P (see FIG. 2) inserted from an insertion hole 11a relatively moves, and a container 20 having an internal space IS in which the core member 10 is accommodated.

The core member 10 is made of an elastic material such as elastomer or gel resin. The volume of the core member 10 is changed by relative inward and outward movements of the penis P in the insertion space ES. For example, when the penis P moves from a base-end side of the insertion space ES toward an inner side of the insertion space ES in the insertion space ES, the core member 10 expands. When the penis P moves from the inner side toward the base-end side in the insertion space ES, the core member 10 contracts.

The container 20 is made of a rigid plastic material (a rigid resin material). The container 20 includes a cylindrical base unit 30 having both ends open in an axis direction of the base unit 30 and a base-end-side (one-end-side) opening portion attached to an end portion of the core member 10 on the insertion-hole-11a side, and a cup-shaped (cylindrical) movable unit 40 made of a rigid plastic material, having a base end (one end) open in an axial direction of the movable unit 40 and a front end (the other end) closed, rotatable around the axis of the movable unit 40 with respect to the base unit 30, and attached in such a manner that the movable unit 40 does not fall off. The base unit 30 supports a portion included in the core member 10 and present near the end portion (the base-end portion) of the core member 10 on the insertion-hole-11a side in a fixed or detachable manner.

At an intermediate position P1 of the sperm collection device 1 in an axial direction of the sperm collection device 1, an inner circumferential surface of the base end of the movable unit 40 overlaps an outer circumferential surface of the front end of the base unit 30. An airflow path AP for air flowing in and out of the container 20 and an adjustment mechanism AD that adjusts the flow rate of air in the airflow path AP are provided in an overlapping part in which the two circumferential surfaces are arranged opposite to each other. The adjustment mechanism AD adjusts the flow rate of air in the airflow path AP based on a rotational angle of the movable unit 40 with respect to the base unit 30.

As illustrated in FIG. 2, when the sperm collection device 1 is used, the penis P (a top end portion PT) relatively reciprocates in the axial direction in the insertion space ES. Since the penis P contacts an inner circumferential surface of the core member 10, stimulations are given to the penis P by frictions (sliding and rubbing) caused by a movement of the penis P in the insertion space ES and ejaculation is facilitated.

As for the use of the sperm collection device 1, a user may apply a viscous liquid lubricant in the insertion space ES and wear a contraceptive (a condom, not illustrated) on the penis P of the user. In this case, semen of the user is ejaculated into the contraceptive and collected. When a lubricant is not used, semen ejaculated in the insertion space ES may be collected.

When the top end portion PT of the penis P relatively moves from the base-end side toward the inner side in the insertion space ES, the core member 10 expands toward an outer-circumference side of the core member 10 due to the penis P within the insertion space ES, as indicated by a dotted line with a reference sign EX in FIG. 2. As a result, air in the internal space IS of the container 20 is discharged out of the container 20 through the adjustment mechanism AD and the airflow path AP.

The pressure of air in the insertion space ES decreases when the top end portion PT of the penis P relatively moves from the inner side toward the base-end side in the insertion space ES. The core member 10 contracts due to the decrease in the pressure of air in the insertion space ES, as indicated by a dotted line with a reference sign CT in FIG. 2.

As a result, the contact of the top end portion PT of the penis P with the inner circumferential surface of the core member 10 becomes stronger, and stronger stimulations are given to the top end portion PT of the penis P. Further, air outside the container 20 flows in the internal space IS of the container 20 through the airflow path AP and the adjustment mechanism AD due to the contraction of the core member 10.

As illustrated in FIG. 1A, the adjustment mechanism AD can change the area of an overlapping part in which one or more of packing-side openings 34c (second openings) of the base unit 30 (a second packing 34) overlap a curved-portion-side opening 42e (a first opening) of the movable unit 40. For example, the adjustment mechanism AD can change the number of packing-side openings 34c (small holes) positioned in an opening range of the curved-portion-side opening 42e to change the area of an overlapping part in which one or more of the packing-side openings 34c overlap the curved-portion-side opening 42e, thereby adjusting the flow rate (ease of the flow of air) of air.

Stimulations given to the top end portion PT of the penis P change based on the air flow rate adjusted by the adjustment mechanism AD. The adjustment of the air flow rate by the adjustment mechanism AD is described later in detail.

As illustrated in FIG. 2, when the air flow rate adjusted by the adjustment mechanism AD is low (when air hardly flows) and the penis P (the top end portion PT) relatively moves from the base-end side toward the inner side in the insertion space ES, the core member 10 expands and air is discharged from the insertion space ES to the internal space IS of the container 20, but is hardly discharged to the outside of the container 20 from the internal space IS of the container 20. Therefore, the core member 10 hardly expands and strong stimulations are given by protrusions 11e to the penis P.

Similarly, when the air flow rate adjusted by the adjustment mechanism AD is low and the penis P relatively moves from the inner side toward the base-end side in the insertion space ES, air hardly flows from the outside of the container 20 to the internal space IS, the core member 10 hardly contracts, the contact of the top end portion PT of the penis P with the inner circumferential surface of the core member 10 is strong, and strong stimulations are given by the protrusions 11e to the penis P.

On the other hand, when the air flow rate adjusted by the adjustment mechanism AD is high (when air easily flows) and the penis P relatively moves from the base-end side toward the inner side in the insertion space ES, air smoothly flows from the internal space IS to the outside of the container 20, and the core member 10 easily expands as compared to the case where the air flow rate is low. As a result, weaker stimulations are given by the protrusions 11e to the penis P as compared to the case where the air flow rate is low.

Similarly, when the air flow rate adjusted by the adjustment mechanism AD is high and the penis P relatively moves from the inner side toward the base-end side in the insertion space ES, air smoothly flows from the outside of the container 20 in the internal space IS, the core member 19 easily contracts, and the contact of the penis P with the inner circumferential surface of the core member 10 is weaker as compared to the case where the air flow rate is low. As a result, weaker stimulations are given by the protrusions 11e to the penis P as compared to the case where the air flow rate is low.

Therefore, as compared to the case where the air flow rate is high, when the air flow rate adjusted by the adjustment mechanism AD is low, stronger stimulations are given to the penis P and ejaculation is facilitated.

As described later, the flow rate (air resistance of the adjustment mechanism AD) of air flowing in and out of the container 20 is adjusted based on a rotational angle of the movable unit 40 with respect to the base unit 30. The adjustment mechanism AD is divided into a base unit 30 side portion and a movable unit 40 side portion and communicates with the outside of the container 20 through the airflow path AP extending along a boundary between the inner circumferential surface of the base end of the movable unit 40 and the outer circumferential surface of the front end of the base unit 30.

In the sperm collection device 1, the airflow path AP and the adjustment mechanism AD are provided in the overlapping part in which the base end (one end) of the movable unit 40 and the front end (the other end) of the base unit 30 are arranged opposite to each other. Therefore, when the sperm collection device 1 is used, the user hardly closes the airflow path AP with his fingers, and it is possible to prevent a change in stimulations that is not intended by the user.

Details of Sperm Collection Device 1 According to First Embodiment

Figure 3A:
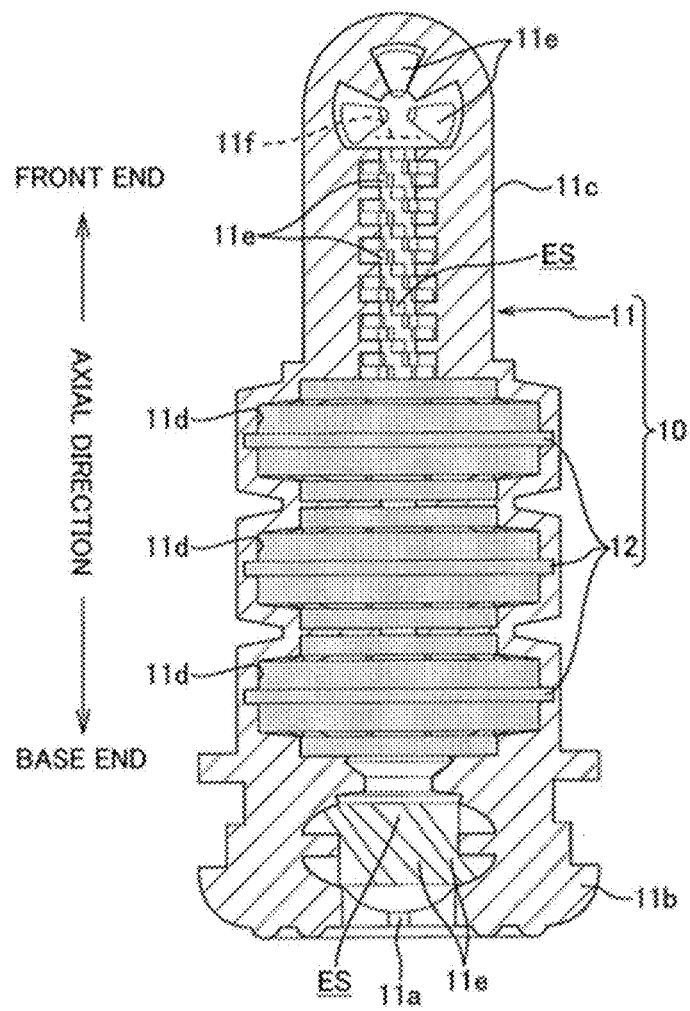
FIG. 3A is an explanatory diagram of the core member.
Figure 3B:
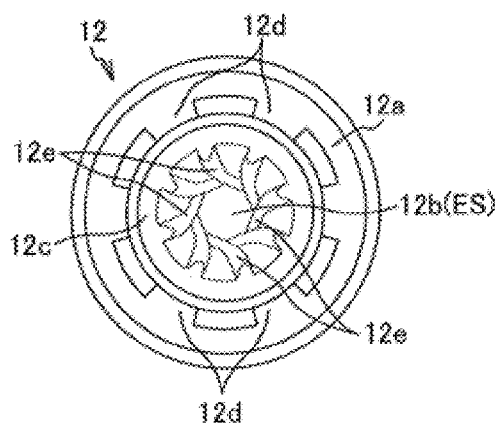
FIG. 3B is an explanatory diagram of ring members.

The sperm collection device 1 according to a first embodiment is described below in detail. First, the core member 10 is described. FIG. 3A is an explanatory diagram of the core member 10, and FIG. 3B is an explanatory diagram of ring members.

Core Member 10

The sperm collection device 1 illustrated in FIG. 2 includes the core member 10 that closely contacts the top end portion PT of the penis P reciprocating in a longitudinal direction of the core member 10 in the insertion space ES and gives stimulations to the top end portion PT of the penis P.

As illustrated in FIG. 3A, the core member 10 includes a core body 11 made of an elastic material (elastomer, gel resin, or the like) with softness imitating a human body (a vagina) and a plurality (for example, three) of ring members 12 made of an elastic material (elastomer, gel resin, or the like) harder than the core body 11 and accommodated in the core body 11.

The core body 11 includes a disk-shaped flange portion 11b having the insertion hole 11a on a central portion of an end surface of the core body 11, a cylindrical portion 11c having the insertion space ES therein, and a plurality (for example, three) of ring storage portions 11d arranged at intervals and closer to the flange portion 11b than to the cylindrical portion 11c.

The flange portion 11b is attached to the base end 30a (a base end 31a of a first cylindrical member 31) of the base unit 30 of the container 20 in an airtight state in a fixed or detachable manner.

The cylindrical portion 11c is a bag body with a front end being closed and has the insertion space ES communicating with the insertion hole 11a. Further, the cylindrical portion 11c has a large number of protrusions 11e on its inner circumferential surface and has an uneven shape. The top end portion PT of the penis P closely contacts the inner circumferential surface of the cylindrical portion 11c in the insertion space ES. Therefore, when the top end portion PT of the penis P relatively inwardly and outwardly moves in the insertion space ES, stimulations are given by the protrusions 11e to the top end portion PT and ejaculation is facilitated.

The ring storage portions 11d accommodate the ring members 12 illustrated in FIG. 3B. Each of the ring members 12 includes an annular outer circumferential portion 12a, a disk-shaped inner circumferential portion 12c having, at its center, an opening 12b through which the penis P is inserted, and a plurality of spoke portions 12d arranged at intervals in a circumferential direction of the ring member 12 and coupling the outer circumferential portion 12a to the inner circumferential portion 12c.

The opening 12b constitutes a part of the insertion space ES (see FIG. 1B). A plurality of projections 12e spirally curved toward the opening 12b are provided on the inner circumferential portion 12c. The projections 12e generate a rotational force in the circumferential direction due to frictions between the projections 12e and the penis P when the penis P moves inwardly and outwardly. Due to the rotational force, the spoke portions 12d become bent in the circumferential direction, the inner circumferential portion 12c rotates, and stimulations are given to the penis P.

Container 20

Figure 4:
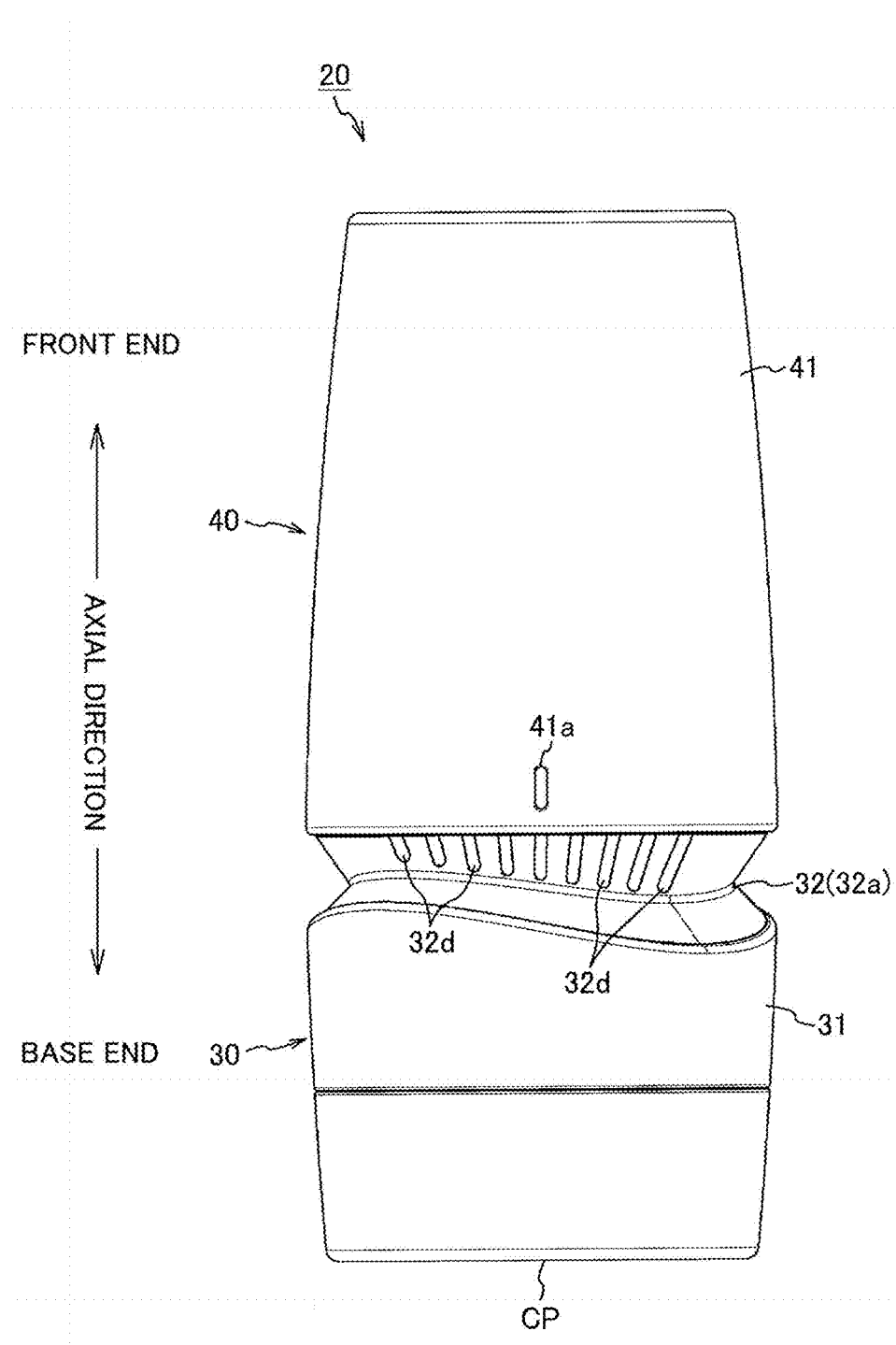
FIG. 4 is a front view of a container.

Next, the container 20 is described. FIG. 4 is a front view of the container 20, FIG. 5 is an exploded perspective view of the container 20, and FIG. 6 is a sectional view of the container 20.

Figure 5:
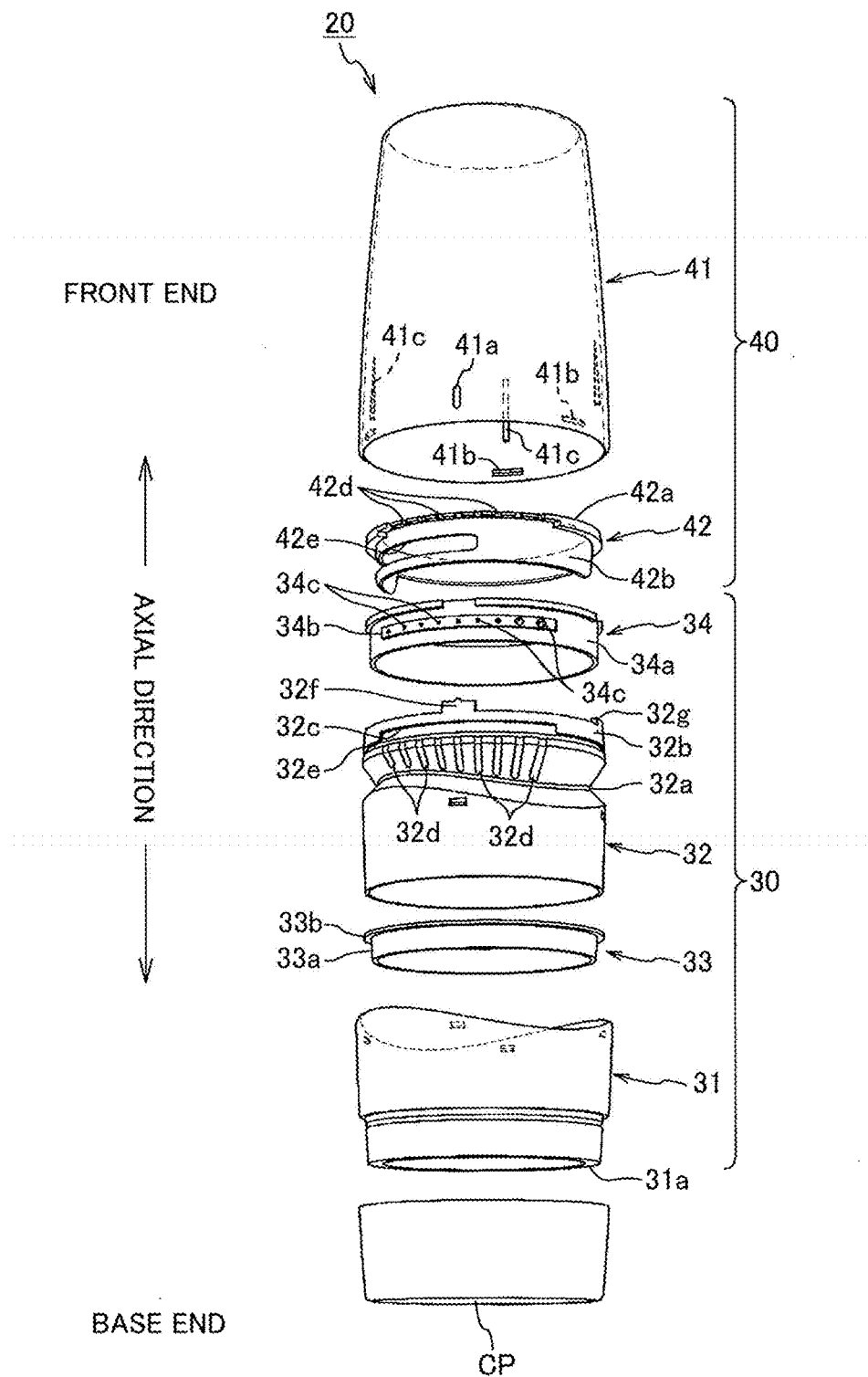
FIG. 5 is an exploded perspective view of the container.
Figure 6:
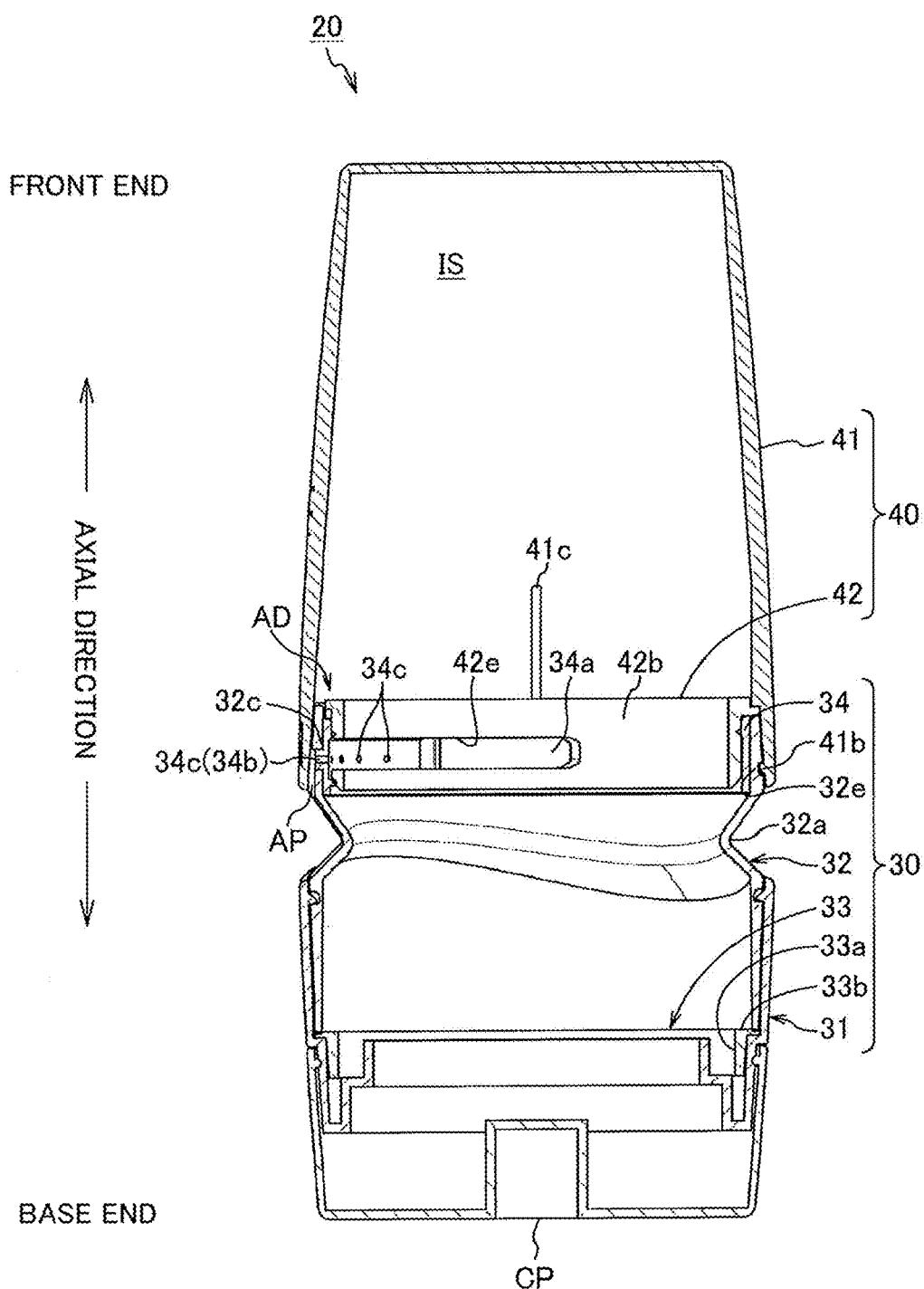
FIG. 6 is a vertical sectional view of the container.

As illustrated in FIGS. 4 to 6, the container 20 includes the cylindrical base unit 30 having both ends open in the axial direction, the cup-shaped (cylindrical) movable unit 40 having the base end open in the axial direction and the front end being closed, rotatable around the axis of the movable unit 40 with respect to the front end of the base unit 30, and attached in such a manner that the movable unit 40 does not fall off, and a cover CP detachably attached to the base end of the base unit 30.

Base Unit 30

As illustrated in FIG. 5, the base unit 30 includes the first cylindrical member 31 having both open ends, a second cylindrical member 32 having both open ends and a substantially-V-shaped recess (a V-shaped groove) 32a provided in an overall circumference of the base unit 30 in the middle in the axis direction, a first packing 33 interposed between the front end of the first cylindrical member 31 and the base end of the second cylindrical member 32, and the second packing 34 attached to the front end of the second cylindrical member 32. Providing the recess 32a enables a finger tip of a user to be easily locked in the recess 32a and reduces inconvenience such as a user dropping the sperm collection device 1.

As illustrated in FIGS. 1A and 1B, the flange portion 11b of the core member 10 is attached to an overall circumference of the base end 31a of the first cylindrical member 31 in an airtight state in a fixed or detachable manner. The base-end portion of the core member 10 slightly protrudes toward an outer side (a user side when the sperm collection device 1 is used) of the container 20 with respect to the base end of the container 20 in an axial direction of the container 20.

As illustrated in FIG. 6, a front-end-side half portion of the first cylindrical member 31 and a base-end-side half portion (a portion present on a base-end side of the second cylindrical member 32 with respect to the recess 32a) of the second cylindrical member 32 are aligned with each other, and an outer circumferential surface of the base-end-side half portion of the second cylindrical member 32 is fitted to and in close contact with an inner circumferential surface of the front-end-side half portion of the first cylindrical member 31.

As illustrated in FIG. 5, the first packing 33 includes a short cylindrical portion 33a and an annular flange portion 33b protruding from the front end of the cylindrical portion 33a toward a laterally outer side of the first packing 33. As illustrated in FIG. 6, the cylindrical portion 33a of the first packing 33 is in close contact with the inner circumferential surface of the first cylindrical member 31. The flange portion 33b is present between the first cylindrical member 31 and the second cylindrical member 32. Since the first packing 33 is interposed between the first cylindrical member 31 and the second cylindrical member 32, the first cylindrical member 31 and the second cylindrical member 32 are connected to each other via the first packing 33 in an airtight state.

In the sperm collection device 1 according to the first embodiment, each of the first cylindrical member 31 and the second cylindrical member 32 is made of a rigid plastic material (for example, the first cylindrical member 31 is made of polycarbonate resin and the second cylindrical member 32 is made of ABS resin), and the first packing 33 is made of synthetic resin (various rubber materials or elastomer with rubber elasticity) having flexibility and sealing property.

As illustrated in FIG. 5, a base-side opening 32c having an elongated shape in a circumferential direction of the second cylindrical member 32 is provided on a side surface (an outer circumferential surface) of a front-end portion 32b of the second cylindrical member 32 and does not extend entirely in the circumferential direction. As described later, a projecting portion 34b of the second packing 34 is fitted in the base-side opening 32c. The internal space IS of the container 20 and the airflow path AP communicate with each other through one or more of the packing-side openings 34c (small holes, second openings) provided in the projecting portion 34b (see FIG. 6).

As illustrated in FIGS. 4 and 5, base-side indices 32d are formed on a surface of the V-shaped recess 32a of the second cylindrical member 32 in a circumferential range corresponding to the base-side opening 32c. The base-side indices 32d are a plurality of grooves (recesses) arranged at intervals in the circumferential direction and having different lengths. Each of the lengths (the lengths of the grooves) of the base-side indices 32d indicates the air flow rate adjusted by the adjustment mechanism AD. For example, the shortest base-side index 32d illustrated on the leftmost side in FIGS. 4 and 5 indicates a state in which the air flow rate is lowest, while the longest base-side index 32d illustrated on the rightmost side in FIGS. 4 and 5 indicates a state in which the air flow rate is highest. The base-side indices 32d (the grooves) extend to the base-side opening 32c, and an inner portion of one or more of the grooves constitutes a portion of the airflow path AP.

Since it suffices as long as the airflow path AP is present between the outer circumferential surface of the base unit 30 and the inner circumferential surface of the movable unit 40, the grooves that constitute a portion of the airflow path AP may be provided on the inner circumferential surface of the base end of the movable unit 40 (a cup member 41).

As illustrated in FIGS. 5 and 6, a locking groove 32e is provided on a front edge (a boundary with the base-side opening 32c) of the V-shaped recess 32a of the second cylindrical member 32 and extends in the circumferential direction. Due to the locking groove 32e, the movable unit 40 is locked to the base unit 30 in such a manner that the movable unit 40 is rotatable around the axis with respect to the base unit 30 and does not fall off (described later).

Either the second cylindrical member 32 or a movable ring 42 may be made of a rigid plastic material having elasticity, the other one of the second cylindrical member 32 and the movable ring 42 may be made of a rigid plastic material not having elasticity, and each of the second cylindrical member 32 and the movable ring 42 may have a fitting structure with a combination of a protrusion and a recess. As indicated in the example of FIG. 5, an elastic portion 32f is provided on the front end of the second cylindrical member 32 and has a protrusion formed on an inner circumference side of the second cylindrical member 32. The protrusion of the elastic portion 32f is fitted in a fitting recess 42d provided in the movable unit 40. Therefore, in the example of FIG. 5, the elastic portion 32f and the fitting recess 42d constitute a fitting structure.

Figure 8:
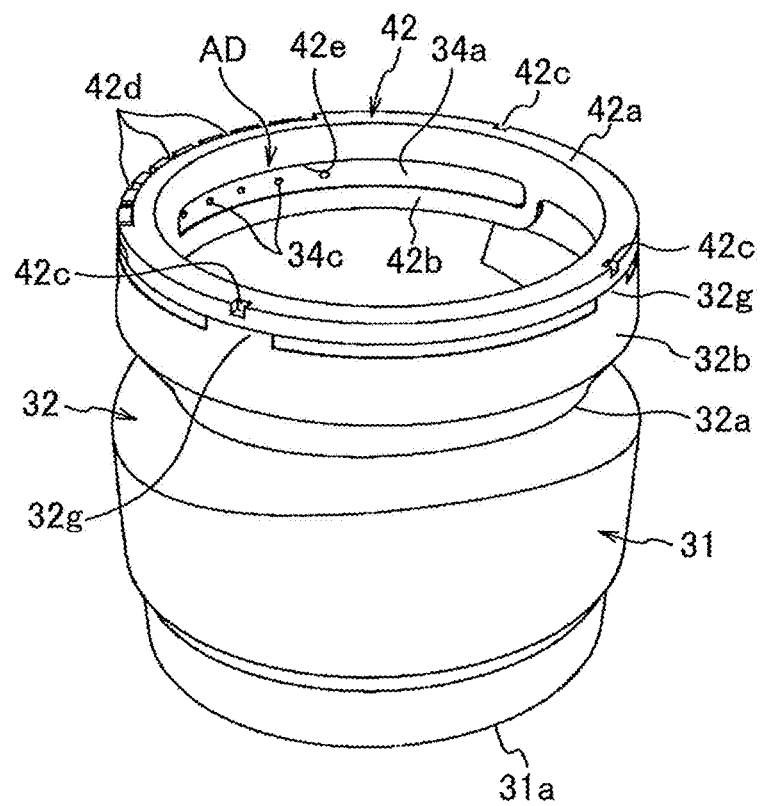
FIG. 8 is a perspective view for explaining an attached state of a movable unit to a base unit.

A plurality of protrusions 32g are provided on a circumferential front edge of the second cylindrical member 32 and arranged at intervals in the circumferential direction. As illustrated in FIG. 8, front ends of the protrusions 32g are in contact with the flange portion 42a from a base-end side of the base unit 30 in the axial direction of the base unit 30 and support the movable ring 42.

As illustrated in FIGS. 5 and 6, the second packing 34 includes a short cylindrical portion 34a in close contact with the inner circumferential surface of the front-end portion 32b of the second cylindrical member 32. A portion (a portion in the opening range) included in the second packing 34 and corresponding to the base-side opening 32c has a thickness larger than the other portions of the second packing 34, and the projecting portion 34b is provided on the concerned portion of the second packing 34 and has an elongated shape in a circumferential direction of the second packing 34. The packing-side openings 34c are provided in the projecting portion 34b. The projecting portion 34b is fitted in the base-side opening 32c.

The packing-side openings 34c are, for example, circular small holes and are arranged at intervals in the circumferential direction. As illustrated in FIG. 5, in the first embodiment, nine packing-side openings 34c are provided, the first to seventh packing-side openings 34c from the left end of FIG. 5 are formed in the same shape (and have the same area), and the eighth and ninth packing-side openings 34c from the left end of FIG. 5 are formed in the same shape (and have the same area) and larger than the first to seventh packing-side openings 34c.

The packing-side openings 34c may be constituted by a plurality of circular small holes having the same size or may be constituted by quadrangular small holes or the like other than circular holes.

In the sperm collection device 1 according to the first embodiment, similarly to the first packing 33, the second packing 34 is made of synthetic resin (for example, various rubber materials or elastomer with rubber elasticity) having flexibility and sealing property.

Moving Unit 40

Figure 7:
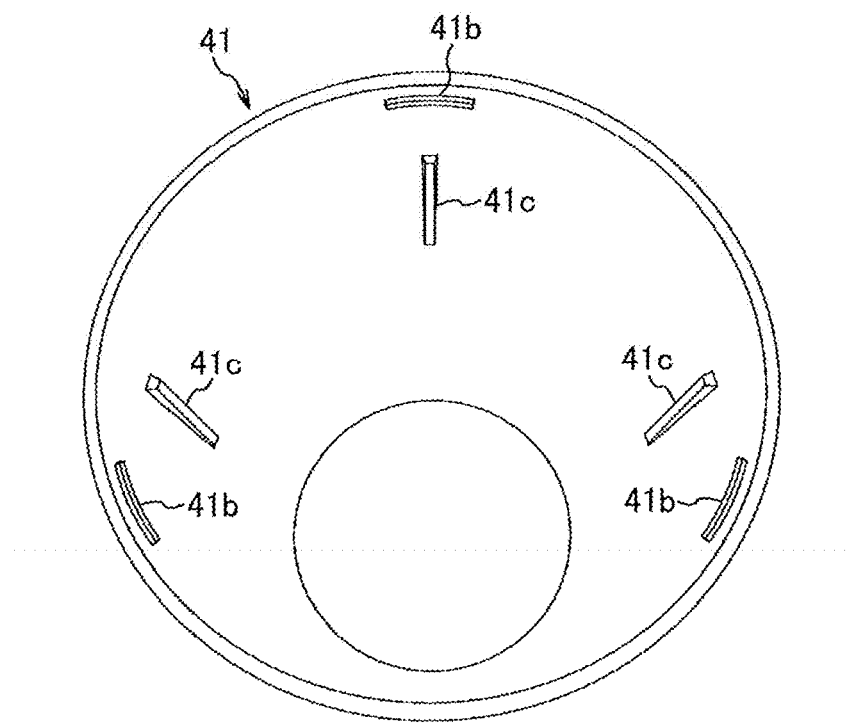
FIG. 7 is a perspective view of a cup member as viewed from an opening side thereof.

Next, the movable unit 40 is described. FIG. 7 is a perspective view of the cup member 41 as viewed from an opening side (a base-end side) of the cup member 41, and FIG. 8 is a perspective view for explaining an attached state of the movable unit 40 to the base unit 30.

As illustrated in FIG. 5, the movable unit 40 includes the cup-shaped cup member 41 having a base end (one end) open and a front end (the other end) closed and having a diameter smaller than that of the base end, and the movable ring 42 attached to an inner circumferential surface of the cup member 41 on the open-base-end side and rotatable integrally with the cup member 41. In the present embodiment, the cup member 41 is made of a rigid plastic material (for example, polycarbonate resin). Since the cup member 41 is made of a resin material of a different type from the material of the second cylindrical member 32, it is possible to reduce the occurrence of an abnormal sound caused by sliding frictions and smoothly slide the cup member 41 and the second cylindrical member 32.

As illustrated in FIG. 4, a movable-side index 41a is provided on an outer circumferential surface of the base end of the cup member 41. The movable-side index 41a is constituted by a protrusion. The position of the movable-side index 41a in a circumferential direction of the cup member 41 is aligned with the position of one of the base-side indices 32d in the circumferential direction of the second cylindrical member 32 based on a rotational angle of the movable unit 40 with respect to the base unit 30. The movable-side index 41a may be formed by printing or may be formed with a sticker.

As described above, each of the lengths (the lengths of the grooves) of the base-side indices 32d indicates the air flow rate adjusted by the adjustment mechanism AD. Therefore, the user can recognize the air flow rate based on the length of a base-side index 32d specified by the movable-side index 41a.

As illustrated in FIG. 7, a first locking protrusion 41b is provided on the inner circumferential surface of the base end of the cup member 41 and extends in the circumferential direction. As illustrated in FIG. 6, the first locking protrusion 41b is locked to the locking groove 32e of the second cylindrical member 32 and can move in the circumferential direction in the locking groove 32e. Therefore, in a state in which the movable unit 40 is attached to the base unit 30, the cup member 41 (the movable unit 40) is attached rotatably around the axis with respect to the second cylindrical member 32 (the base unit 30) in such a manner that the cup member 41 (the movable unit 40) does not fall off.

As illustrated in FIG. 7, a plurality of second locking protrusions 41c are provided on the inner circumferential surface of the cup member 41 and have an elongated shape in an axial direction (a longitudinal direction) of the cup member 41. In the example illustrated in FIG. 7, three second locking protrusions 41c are arranged at approximately 90-degree intervals in the circumferential direction. Lower ends of the second locking protrusions 41c are fitted in locking grooves 42c (FIG. 8) provided in the movable ring 42. Therefore, the movable ring 42 rotates around the axis integrally with the cup member 41.

As illustrated in FIGS. 5 and 8, the movable ring 42 includes an annular flange portion 42a in contact with the front end (the second packing 34) of the base unit 30 and a curved portion 42b integrated with the flange portion 42a. The movable ring 42 is made of a rigid plastic material (for example, polyacetal resin or polyamide resin) having elasticity.

The notch-like locking grooves 42c and the fitting recesses 42d are provided in the flange portion 42a. Base ends of the second locking protrusions 41c provided on the inner circumferential surface of the cup member 41 are fitted in the notch-like locking grooves 42c. The elastic portion 32f (the protrusion) provided in the second cylindrical member 32 is fitted in any of the fitting recesses 42d. In the example illustrated in FIG. 8, similarly to the second locking protrusions 41c, three locking grooves 42c are arranged at intervals in a circumferential direction of the movable ring 42, and the fitting recesses 42d are arranged at intervals in the circumferential direction in such a manner that the number of the fitting recesses 42d is the same as the number of base-side indices 32d.

As described above, when the base ends of the second locking protrusions 41c are fitted in the corresponding locking grooves 42c, the movable ring 42 is rotatable around the axis integrally with the cup member 41. When the protrusion of the elastic portion 32f is repeatedly fitted in and separated from any of the fitting recesses 42d during the rotation of the movable unit 40, rotational resistance increases and decreases (click feeling).

This click feeling enables a user to recognize, based on tactile sensation, that the movable unit 40 has rotated and the amount of air has changed when the sperm collection device 1 is used. Further, it is possible to reduce inconvenience such as rotation of the movable unit 40 that is not intended by the user.

The curved portion 42b is a plate-shaped member having an elongated shape in the circumferential direction and curved along the inner circumferential surface (the inner circumferential surface of the second packing 34) of the front end of the base unit 30. When the movable unit 40 (the cup member 41) rotates around its axis, the curved portion 42b moves along the inner circumferential surface of the front end of the base unit 30 in the circumferential direction.

The curved-portion-side opening 42e (the first opening) is provided in the curved portion 42b and has an elongated shape in the circumferential direction. The curved-portion-side opening 42e has a shape enabling the plurality of packing-side openings 34c (the plurality of second openings) provided in the second packing 34 to be positioned in the opening range.

As illustrated in FIG. 6, in a state in which the movable unit 40 is attached to the base unit 30, the inner circumferential surface of the base end of the cup member 41 overlaps the outer circumferential surface of the front end of the second cylindrical member 32. The second packing 34 is interposed between the curved portion 42b and the second cylindrical member 32 in the overlapping part in which the curved portion 42b and the second cylindrical member 32 are arranged opposite to each other. The portions included in the second packing 34 and excluding the packing-side openings 34c are attached in an airtight state.

A portion of the airflow path AP is constituted by one or more of the base-side indices 32d between the inner circumferential surface of the base end of the cup member 41 and the outer circumferential surface of the front end of the second cylindrical member 32. Therefore, the internal space IS communicates with the outside of the container 20 through one or more (the adjustment mechanism AD) of the packing-side openings 34c and the airflow path AP.

Adjustment Mechanism AD

The adjustment mechanism AD adjusts the flow rate (ease of the flow of air) of air flowing in and out of the container 20. In the sperm collection device 1 according to the first embodiment, the adjustment mechanism AD is constituted by a front-end portion (the front-end portion 32b of the second cylindrical member 32 and the packing-side openings 34c) of the base unit 30 and a base-end portion (the movable ring 42 and the curved-portion-side opening 42e) of the movable unit 40.

Figure 9A:
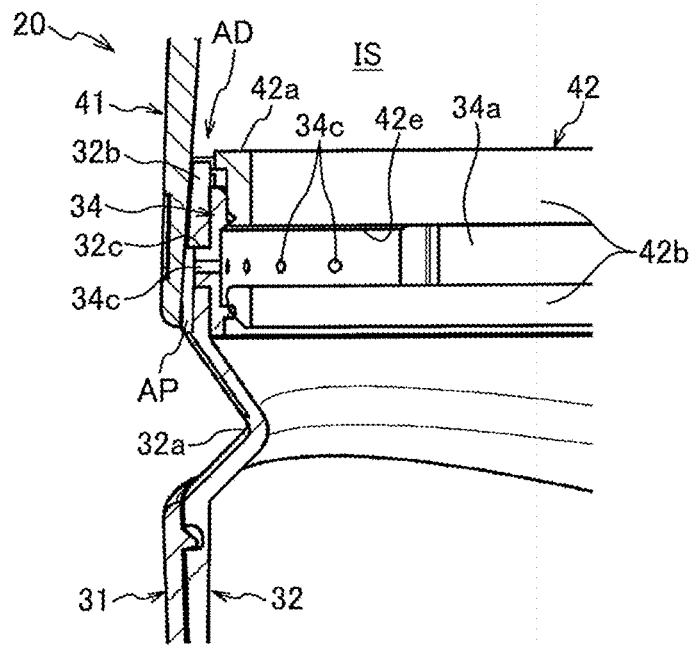
FIG. 9A is a partially enlarged sectional view of the vicinity of an adjustment mechanism.

The adjustment mechanism AD is described below. FIG. 9A is a partially enlarged sectional view of the vicinity of the adjustment mechanism AD, FIG. 9B is an explanatory diagram of a flow of air in the vicinity of the adjustment mechanism AD, FIG. 10 is an explanatory diagram of a rotation operation performed on the movable unit 40, FIG. 11A is an explanatory diagram of positional relationships between the curved-portion-side opening 42e and the packing-side openings 34c when the air flow rate is adjusted by the adjustment mechanism AD to the minimum level, and FIG. 11B is an explanatory diagram of positional relationships between the curved-portion-side opening 42e and the packing-side openings 34c when the air flow rate is adjusted by the adjustment mechanism AD to the maximum level.

Figure 9B:
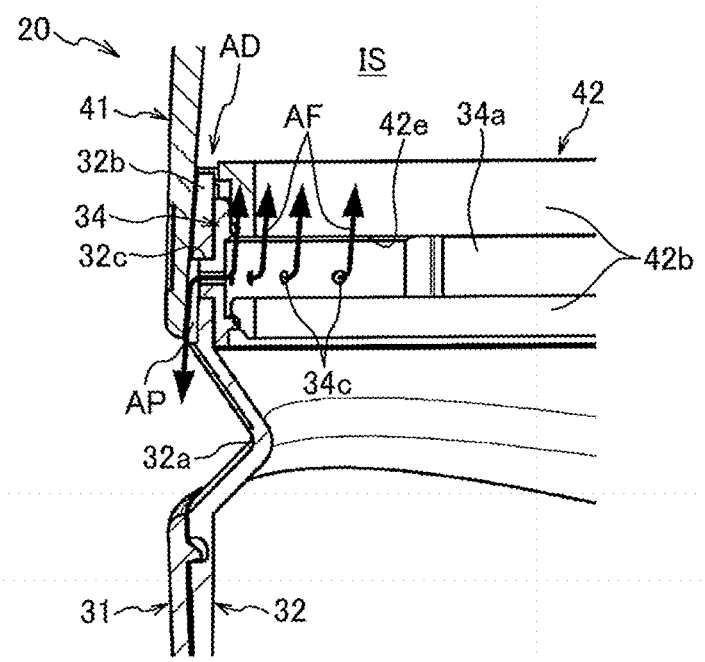
FIG. 9B is an explanatory diagram of a flow of air in the vicinity of the adjustment mechanism.

As illustrated in FIG. 9A, when the curved-portion-side opening 42e is moved in the circumferential direction and one or more of the packing-side openings 34c are positioned in the opening range of the curved-portion-side opening 42e, the internal space IS of the container 20 communicates with the outside of the container 20 through the airflow path AP, the one or more packing-side openings 34c, and the curved-portion-side opening 42e, as indicated by arrows AF in FIG. 9B. In this case, the flow rate of air flowing in and out of the container 20 is determined based on the total of opening areas of the packing-side openings 34c positioned in the opening range of the curved-portion-side opening 42e, that is, based on the number (the number of small holes) of packing-side openings 34c positioned in the opening range of the curved-portion-side opening 42e.

Figure 10:
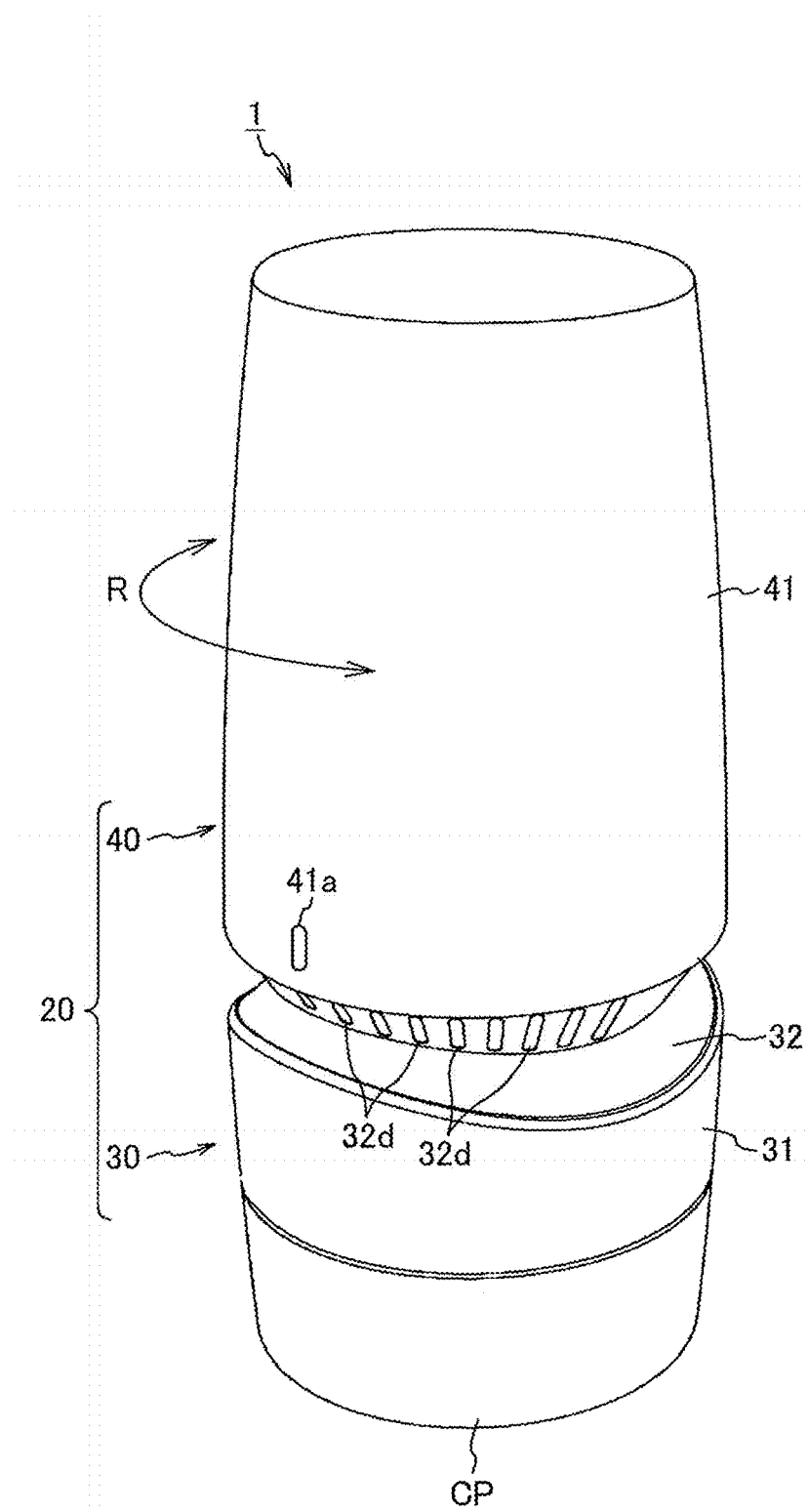
FIG. 10 is an explanatory diagram of a rotation operation performed on the movable unit.

As illustrated in FIG. 10, the flow rate of air flowing in and out of the container 20 can be adjusted by rotating the movable unit 40 around the axis with respect to the base unit 30. That is, the curved portion 42b can be moved in the circumferential direction by the rotation of the movable unit 40 to change a relative position of the curved-portion-side opening 42e in the circumferential direction of the movable ring 42 to the position of the packing-side openings 34c in the circumferential direction of the second packing 34.

Figure 11A:
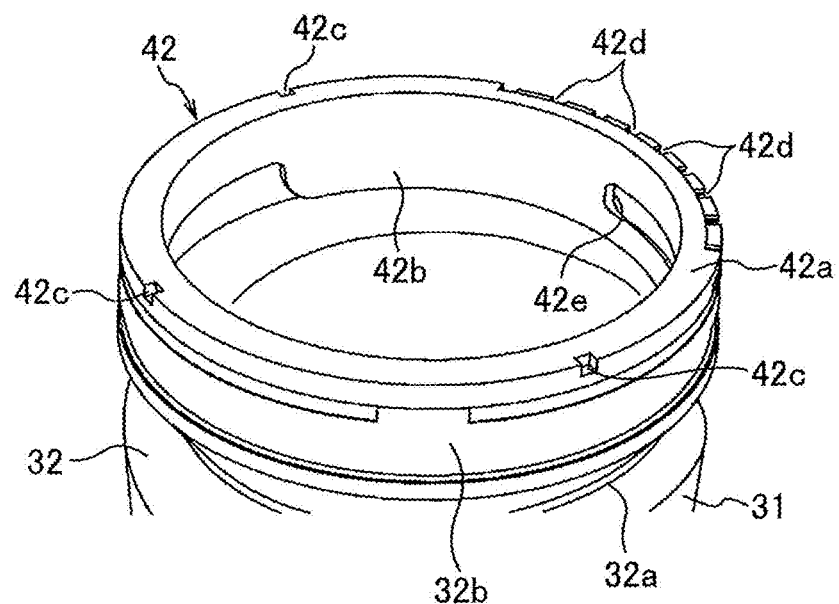
FIG. 11A is an explanatory diagram of positional relationships between a curved-portion-side opening and packing-side openings when the air flow rate is adjusted by the adjustment mechanism to the minimum level.
Figure 11B:
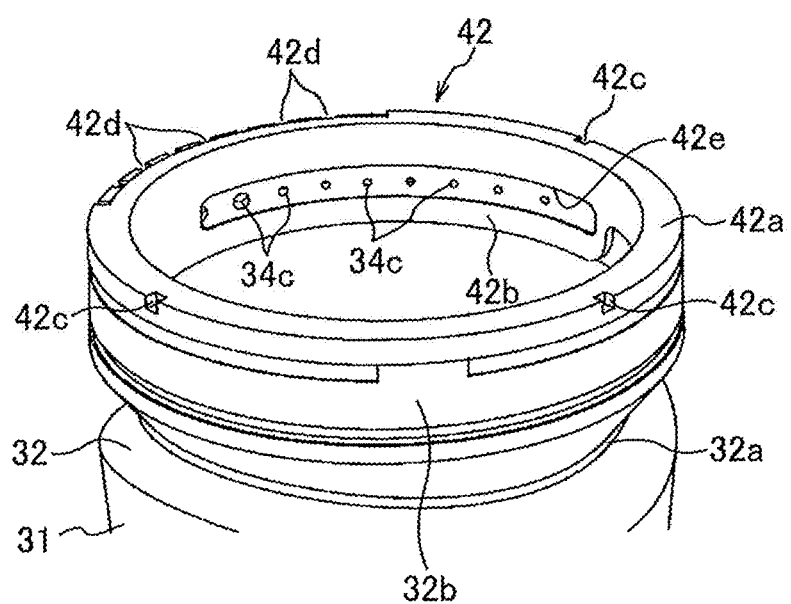
FIG. 11B is an explanatory diagram of positional relationships between the curved-portion-side opening and the packing-side openings when the air flow rate is adjusted by the adjustment mechanism to the maximum level.

For example, in the state illustrated in FIG. 11A, all the packing-side openings 34c are not positioned in the opening range of the curved-portion-side opening 42e, and it is hardest to cause air to flow. On the other hand, in the state illustrated in FIG. 11B, all the packing-side openings 34c are positioned in the opening range of the curved-portion-side opening 42e, so that air flow most easily in this case.

In an intermediate state between the state illustrated in FIG. 11A and the state illustrated in FIG. 11B, the flow rate of air varies depending on the total (the number of small holes) of opening areas of packing-side openings 34c positioned in the opening range of the curved-portion-side opening 42e.

Summary of First Embodiment

The sperm collection device 1 according to the first embodiment has the airflow path AP in the overlapping part (opposing portion) in which the inner circumferential surface of the base end of the movable unit 40 and the outer circumferential surface of the front end of the base unit 30 overlap each other. The adjustment mechanism AD that adjusts the flow rate of air flowing in and out of the container 20 is present between the airflow path AP and the internal space IS of the container 20 and can adjust the flow rate of air based on a rotational angle of the movable unit 40 with respect to the base unit 30. Therefore, the user hardly unintentionally closes the airflow path AP with his fingers, and it is possible to prevent a change in stimulations given to the penis P that is not intended by the user.

Sperm Collection Device 1A According to Second Embodiment

In the sperm collection device 1 according to the first embodiment described above, stimulations to be given to the top end portion PT of the penis P are adjusted by changing air resistance of the adjustment mechanism AD based on the total (the number of packing-side openings 34c) of opening areas of the packing-side openings 34c positioned in the opening range of the curved-portion-side opening 42e. However, the sperm collection device 1 is not limited to this configuration.

Figure 12:
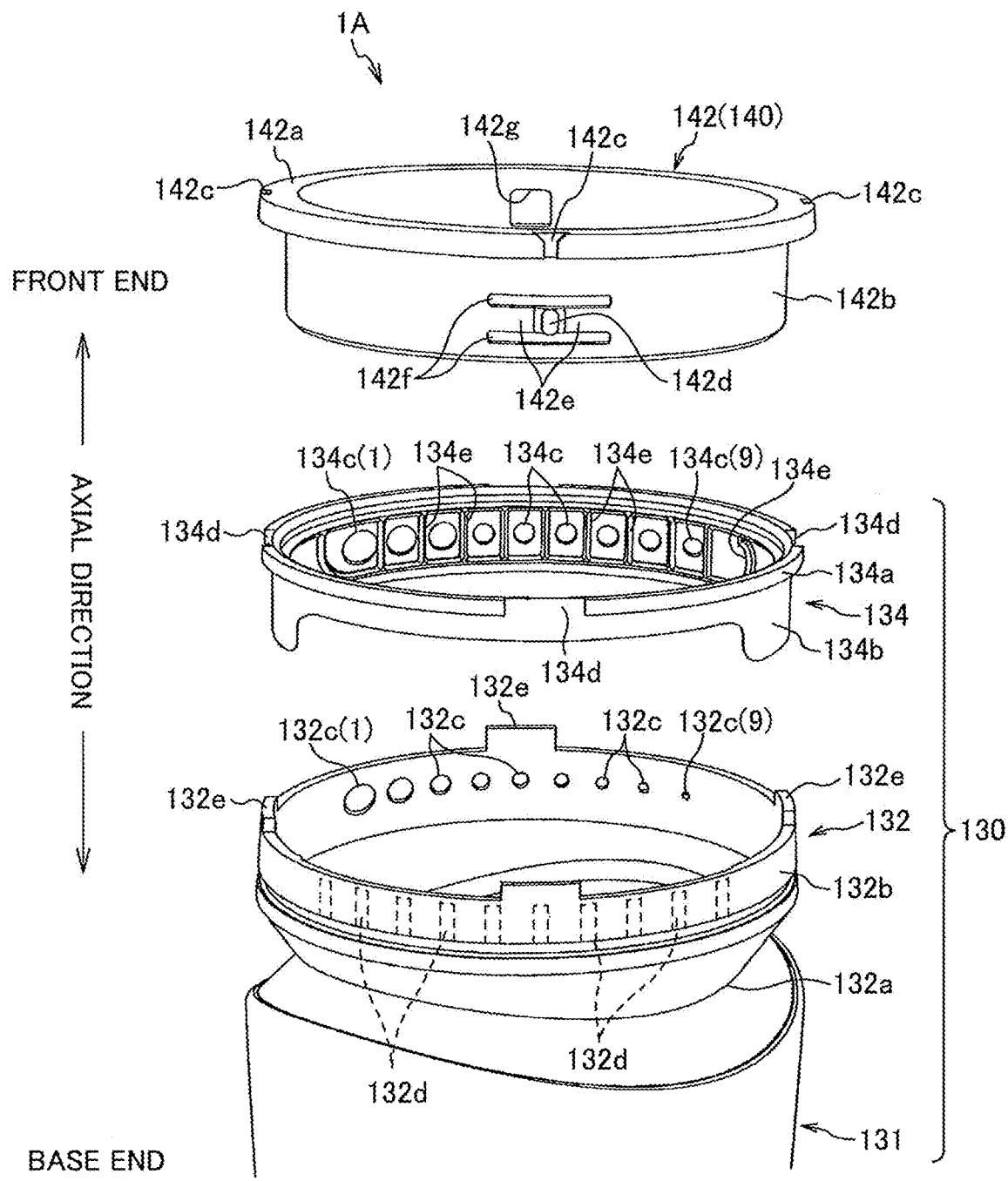
FIG. 12 is an exploded perspective view for explaining relevant parts of a sperm collection device according to a second embodiment.

For example, as illustrated in FIG. 12, a plurality of types of openings having different opening areas may constitute packing-side openings 134c (second openings) and base-side openings 132c (second openings), and any of combinations of the packing-side openings 134c and the base-side openings 132c may be positioned on an inner side of a movable cylinder-side opening 142g (a first opening) based on a rotational angle of a movable unit 140 with respect to a base unit 130.

Figure 13A:
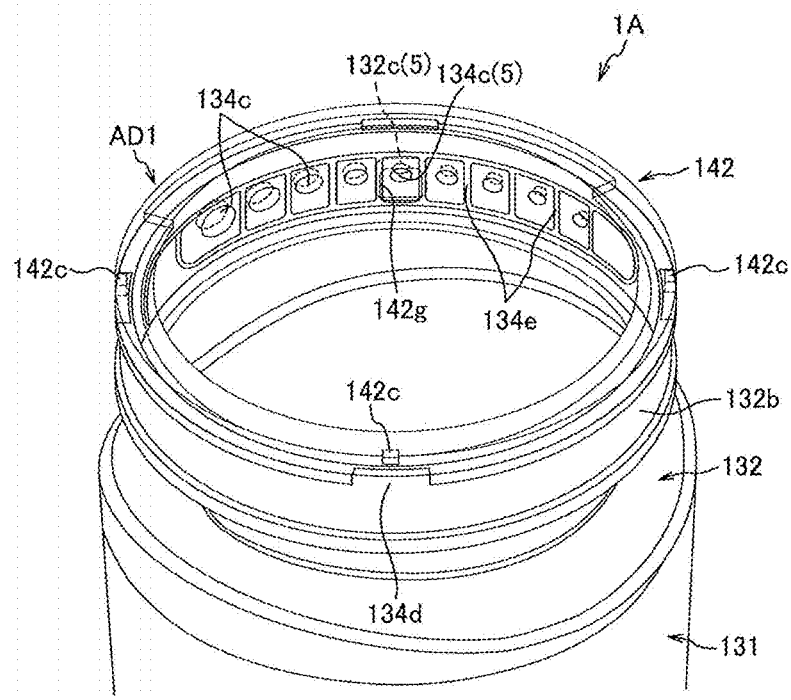
FIG. 13A is an explanatory diagram of a state when one of openings constituting packing-side openings is selected.
Figure 13B:
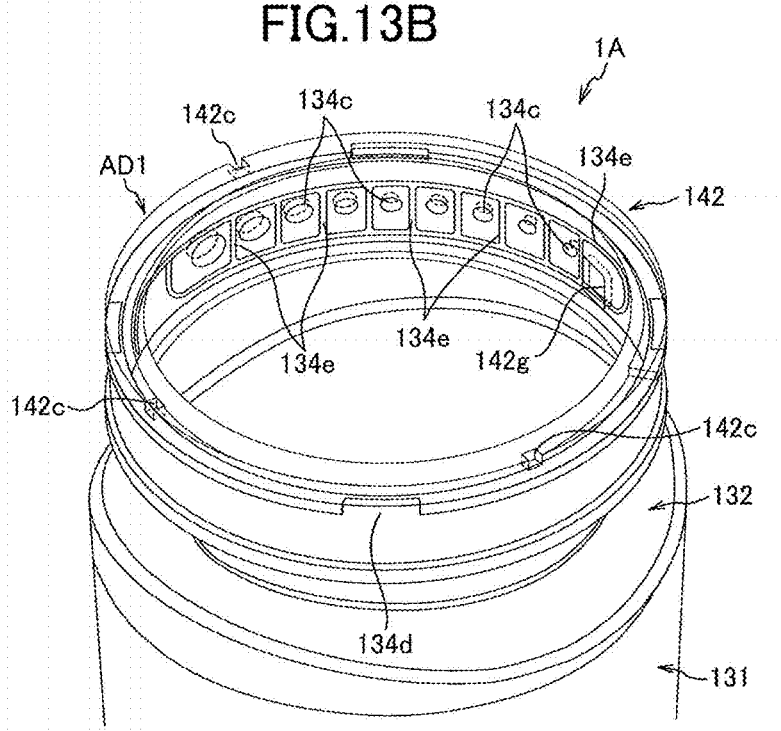
FIG. 13B is an explanatory diagram of a state when any of the packing-side openings is not selected.

A sperm collection device 1A configured in the foregoing manner according to a second embodiment is described below. FIG. 12 is an exploded perspective view for explaining relevant parts of the sperm collection device 1A according to the second embodiment, FIG. 13A is an explanatory diagram of a state when one of the packing-side openings 134c is selected, and FIG. 13B is an explanatory diagram of a state when any of the packing-side openings 134c is not selected.

The sperm collection device 1A illustrated in FIG. 12 includes the plurality of base-side openings 132c (the second openings) provided on a side surface of a front end 132b of the base unit 130 (a second cylindrical member 132), the plurality of packing-side openings 134c (the second openings) provided in a second packing 134, and the single movable cylinder-side opening 142g (the first opening) provided in a movable ring 142.

In the sperm collection device 1A, constituent elements identical to those of the sperm collection device 1 according to the first embodiment are denoted by like reference signs and explanations thereof are omitted. In addition, constituent elements of the sperm collection device 1A not illustrated in the drawings are identical to those of the sperm collection device 1 according to the first embodiment and thus explanations thereof are omitted.

The base unit 130 includes a first cylindrical member 131, the second cylindrical member 132, a first packing (not illustrated), and a second packing 134, similarly to the base unit 30 described in the first embodiment. The configurations of the first cylindrical member 131 and the first packing are identical to those of the first cylindrical member 31 and the first packing 33, and thus explanations thereof are omitted.

The second cylindrical member 132 has both ends open in an axial direction of the base unit 130 and has a V-shaped recess 132a provided in an overall circumference of the second cylindrical member 132 in the middle in the axial direction. A portion included in the second cylindrical member 132 and present on a base-end side of the second cylindrical member 132 with respect to the recess 132a is fitted to an inner circumferential side portion of a front-end-side half portion of the first cylindrical member 131. The first packing is interposed between the second cylindrical member 132 and the first cylindrical member 131 and connects the cylindrical members 131 and 132 to each other in an airtight state, similarly to the first packing 33 described in the first embodiment.

The plurality of base-side openings 132c are arranged at intervals in the circumferential direction on a side surface of the front end 132b of the second cylindrical member 132. In the example illustrated in FIG. 12, nine base-side openings 132c are constituted by annular small holes and arranged at intervals in the circumferential direction and have mutually different opening areas, the base-side opening 132c(1) illustrated on the leftmost side has the largest opening area, and the base-side opening 132c(9) illustrated on the rightmost side has the smallest opening area.

Fitting recesses 132d are constituted by a plurality of grooves (recesses) and arranged in the circumferential direction on an inner circumferential surface of the front end 132b of the cylindrical member 132 at positions opposite to the base-side openings 132c. Further, a plurality of protrusions 132e serving as a stopper for rotation of the second packing 134 are arranged at intervals in the circumferential direction on the front end 132b of the second cylindrical member 132. In the example illustrated in FIG. 12, four protrusions 132e are arranged at 90-degree intervals.

The second packing 134 includes a ring-shaped portion 134a, a curved portion 134b integrated with the ring-shaped portion 134 and having an elongated shape in a circumferential direction of the second packing 134, and the packing-side openings 134c provided in the curved portion 134b. The second packing 134 described in the second embodiment is made of synthetic resin (for example, various rubber materials or elastomer with rubber elasticity) having flexibility and sealing property, similarly to the second packing 34 described in the first embodiment.

The ring-shaped portion 134a is placed on a front-end surface of the second cylindrical member 132. Notches 134d are arranged at 90-degree intervals in the circumferential direction and fitted to the protrusions 132e provided on the front end of the second cylindrical member 132. The curved portion 134b is aligned with an inner circumferential surface of the front end of the second cylindrical member 132 and has a shape (for example, a horizontally rectangular shape) enabling the curved portion 134b to cover all the base-side openings 132c.

Similarly to the base-side openings 132c, the plurality of packing-side openings 134c are arranged at intervals in the circumferential direction. In the example illustrated in FIG. 12, the packing-side openings 134c are constituted by nine circular holes with different opening areas, the packing-side opening 134c(1) illustrated on the leftmost side has the largest opening area, and the packing-side opening 134c(9) illustrated on the rightmost side has the smallest opening area. In the second embodiment, the shapes (the opening areas) and positions of the packing-side openings 134c match the shapes (the opening areas) and positions of the base-side openings 132c corresponding to the packing-side openings 134c.

Further, substantially-quadrangular ribs 134e are formed on an inner circumferential surface of the curved portion 134b and surround the respective packing-side openings 134c. Any packing-side opening 134c is not present on an inner circumference of the rib 134e illustrated on the rightmost side in FIG. 12.

The movable ring 142 includes an annular flange portion 142a in contact with the front end (the second packing 134) of the base unit 130, and a movable cylinder 142b provided on the flange portion 142a. The flange portion 142a has notch-like locking grooves 142c fitted to base ends of the second locking protrusions 41c provided on the inner circumferential surface of the cup member 41. Therefore, the movable ring 142 rotates around the axis of the movable unit 140 integrally with the cup member 41.

The movable cylinder 142b has the movable-cylinder-side opening 142g (the first opening). The movable-cylinder-side opening 142g is a single rectangular opening and one of the packing-side openings 134c can be positioned on an inner side of the movable-cylinder-side opening 142g.

A fitting protrusion 142d is formed on the movable cylinder 142b at a position 180 degrees opposite to the position of the movable-cylinder-side opening 142g of the movable cylinder 142b in a circumferential direction of the movable ring 142. The fitting protrusion 142d protrudes toward an outer side of the movable ring 142 from a central portion of a plate-like spring portion 142e in the circumferential direction. The spring portion 142 has an elongated shape in the circumferential direction. In the present embodiment, the plate-like spring portion 142e is constituted by two slits 142f having an elongated shape in the circumferential direction and arranged at an interval in an axial direction of the movable unit 140.

When any of the packing-side openings 134c is positioned on the inner side of the movable cylinder-side opening 142g, the fitting protrusion 142d is fitted in one of the fitting recesses 132d provided on the inner circumferential surface of the front end of the second cylindrical member 132. When the fitting protrusion 142d fitted in the fitting recess 132d moves to an adjacent fitting recess 132d, rotational resistance of the movable unit 140 increases and decreases (click feeling).

This click feeling enables a user to recognize, based on tactile sensation, that the movable unit 140 has rotated and the amount of air has changed. Further, it is possible to reduce inconvenience such as rotation of the movable unit 140 that is not intended by the user.

In the sperm collection device 1A according to the second embodiment, the second packing 134 is attached to the second cylindrical member 132 in a state in which an outer circumferential surface of the curved portion 134b of the second packing 134 is arranged opposite to the inner circumferential surface of the front end of the second cylindrical member 132 and in which the positions of the base-side openings 132c (second openings) in the circumferential direction of the second cylindrical member 132 match the positions of the packing-side openings 134c (second openings) in the circumferential direction of the second packing 134.

Further, since the second packing 134 is attached to the second cylindrical member 132 in a state in which an outer circumferential surface of the movable cylinder 142b rotatable in the circumferential direction is arranged opposite to the inner circumferential surface of the curved portion 134b of the second packing 134, any of the packing-side openings 134c is positioned on the inner side of the movable cylinder-side opening 142g (the first opening).

In the example illustrated in FIG. 13A, the fifth packing-side opening 134c(5) from the left end of FIG. 13A is positioned on the inner side of the movable cylinder-side opening 142g. Therefore, the movable-cylinder-side opening 142g, the packing-side opening 134c(5), and the base-side opening 132c(5) communicate with each other, and air flows in and out of the container 20 at a flow rate based on opening areas (flow path resistance) of the openings 142g, 134c(5), and 132(5).

In the example illustrated in FIG. 13B, the movable unit 40 (the cup member 41 and the movable ring 142) is rotated clockwise from the state illustrated in FIG. 13A and the movable cylinder-side opening 142g is positioned on the inner circumference of the rib 134e on which any packing-side opening 134c is not present. In this state, air flows only through a gap between the movable unit 40 and the base unit 30 and a gap between the insertion space ES and the penis P, and stimulations given to the penis P are strongest.

Since the opening areas of the plurality of packing-side openings 134c are different and the opening areas of the plurality of base-side openings 132c are different, the flow rate of air flowing in and out of the container 20 is adjusted based on a rotational angle of the movable unit 40 with respect to the base unit 30. Therefore, it is possible to adjust the strength of stimulations to be given to the penis P based on the rotational angle.

Sperm Collection Device 1B According to Third Embodiment

The sperm collection device 1A according to the second embodiment is configured that one of combinations (second openings) of the packing-side openings 134c having different opening areas and the base-side openings 132c having different opening areas is selected for the single movable cylinder-side opening 142g (first opening). However, the sperm collection device 1A is not limited to this configuration.

Figures 14A, 14B:
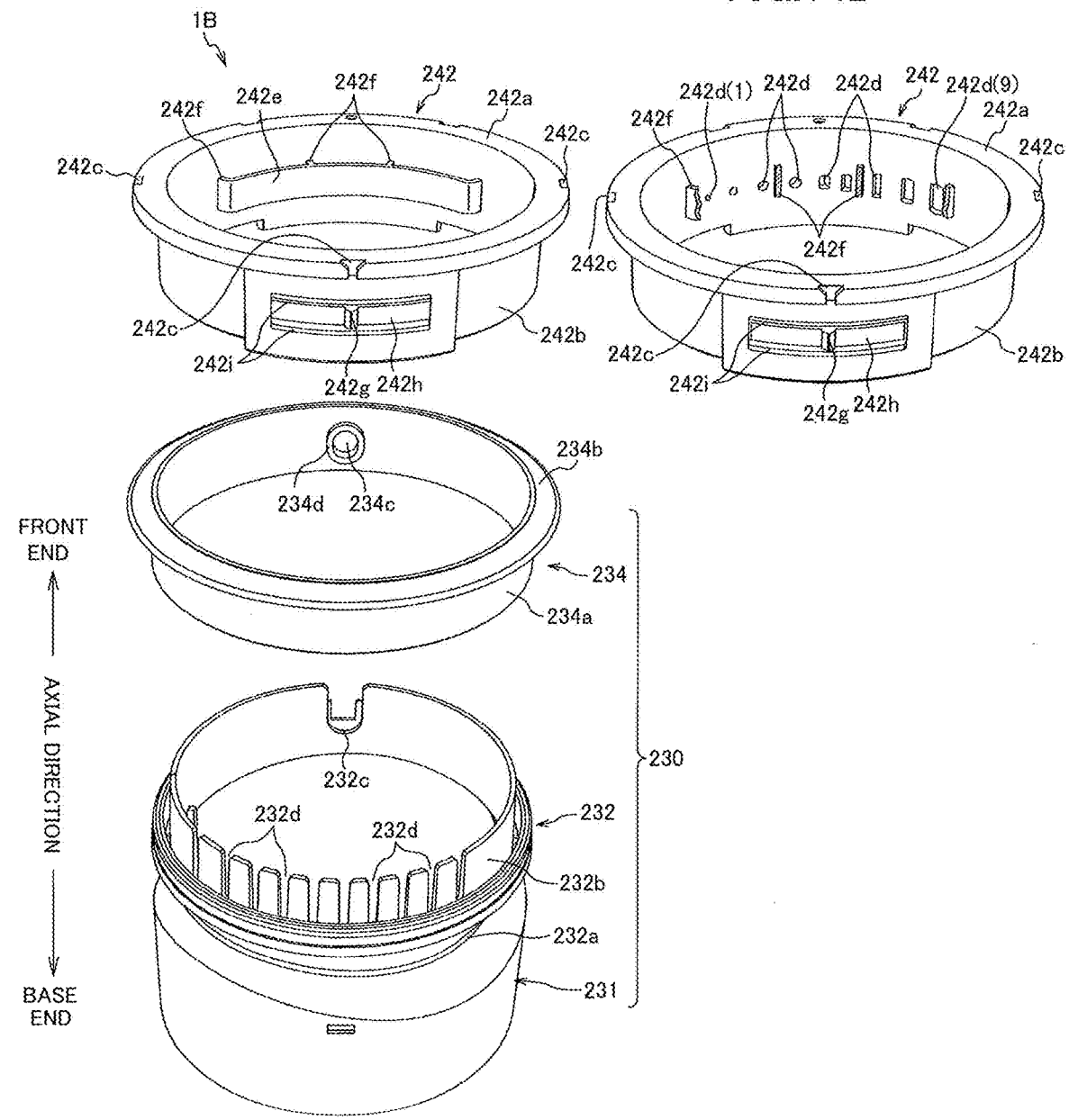
FIG. 14A is an exploded perspective view for explaining relevant parts of a sperm collection device according to a third embodiment.
FIG. 14B is an explanatory diagram of a movable cylinder-side openings formed in a movable ring.

For example, as illustrated in FIGS. 14A and 14B, one of a plurality of movable-cylinder-side openings 242d (first openings) having different opening areas may be selectively positioned on an inner side of one packing-side opening 234c (a second opening).

Figure 15:
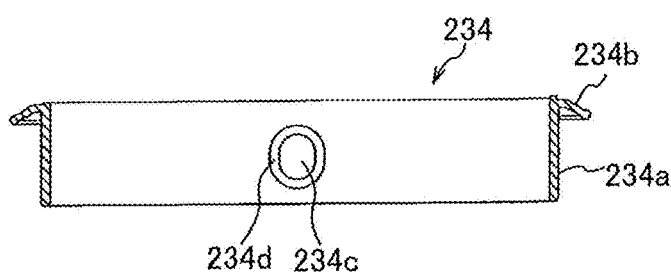
FIG. 15 is a sectional view of a second packing.
Figure 16A:
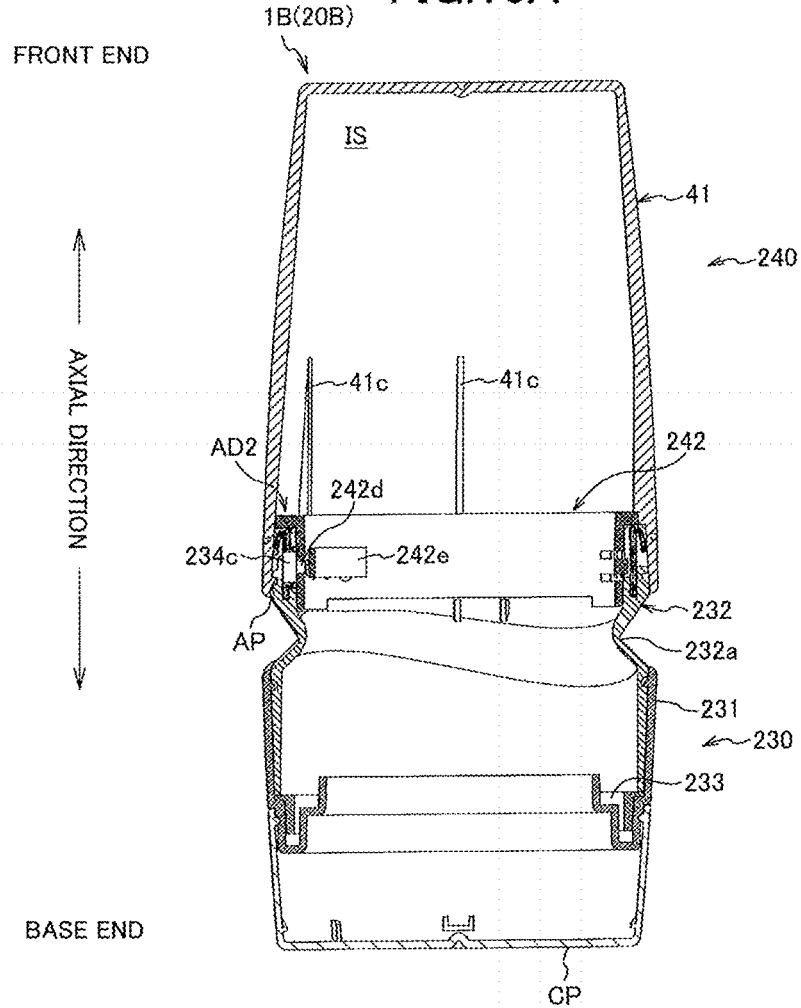
FIG. 16A is a vertical sectional view of a container.
Figure 16B:
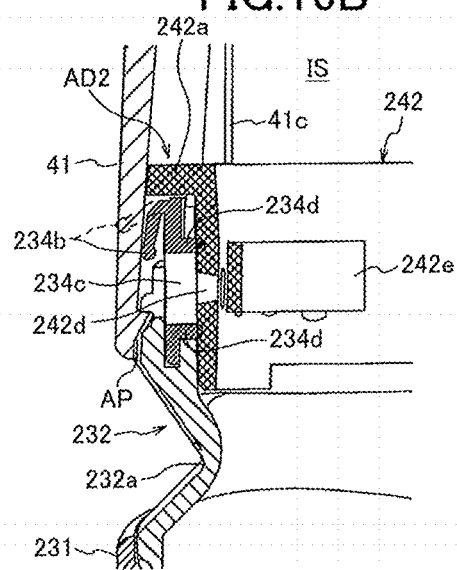
FIG. 16B is a partially enlarged sectional view of the vicinity of an adjustment mechanism.

A sperm collection device 1B configured in the foregoing manner according to a third embodiment is described below. FIG. 14A is an exploded perspective view for explaining relevant parts of the sperm collection device 1B according to the third embodiment, FIG. 14B is an explanatory diagram of the movable cylinder-side openings 242d formed in a movable ring 242, FIG. 15 is a sectional view of the second packing 234, FIG. 16A is a vertical sectional view of a container 20B, and FIG. 16B is a partially enlarged sectional view of the vicinity of an adjustment mechanism AD2.

The sperm collection device 1B illustrated in FIG. 14A includes a base-side groove 232c provided in a front end 232b of a base unit 230 (a second cylindrical member 232), the packing-side opening 234c (the second opening) provided in the second packing 234, and the plurality of movable cylinder-side openings 242d (first openings) provided in the movable ring 242.

In the sperm collection device 1B according to the third embodiment, constituent elements identical to those of the sperm collection device 1 according to the first embodiment are denoted by like reference signs and explanations thereof are omitted. In addition, constituent elements of the sperm collection device 1B not illustrated in the drawings are identical to those of the sperm collection device 1 according to the first embodiment and thus explanations thereof are omitted.

Similarly to the base unit 30 described in the first embodiment, the base unit 230 includes a first cylindrical member 231, the second cylindrical member 232, a first packing 233 (see FIG. 16A), and the second packing 234. The configurations of the first cylindrical member 231 and the first packing 233 are identical to those of the first cylindrical member 31 and the first packing 33, and thus explanations thereof are omitted.

The second cylindrical member 232 has both ends open in an axial direction of the base unit 230 and has a substantially-V-shaped recess 232a provided in an overall circumference of the second cylindrical member 232 in the middle in the axial direction. A portion included in the second cylindrical member 232 and present on a base-end side of the second cylindrical member 232 with respect to the recess 232a is fitted to an inner-circumferential-portion of a front-end-side half portion of the first cylindrical member 231. The first packing 233 is interposed between the base end of the second cylindrical member 232 and the first cylindrical member 231 and connects the cylindrical members 231 and 232 to each other in an airtight state, as illustrated in FIG. 16A.

The base-side groove 232c provided in the front end 232b of the second cylindrical member 232 is constituted by a single groove with an open front end. In the example of FIG. 14A, the base-end groove 232c is constituted by a U-shaped groove, but is not limited to this shape. For example, the base-side groove 232c may be constituted by a quadrangular groove with an open front end.

A plurality of fitting slits 232d are provided in the front end 232b of the second cylindrical member 232 at positions opposite to the base-side groove 232c in the circumferential direction. Each of the quadrangular fitting slits 232d has an open front end and has an elongated shape in the axial direction. In this example, ten fitting slits 232d are arranged at intervals in the circumferential direction.

As illustrated in FIGS. 14A and 15, the second packing 234 includes a cylindrical portion 234a, a ring-shaped portion 234b integrated with a front end of the cylindrical portion 234a, and the packing-side opening 234c provided on a side surface of the cylindrical portion 234a. The second packing 234 described in the third embodiment is made of synthetic resin (various rubber materials or elastomer with rubber elasticity) having flexibility and sealing property, similarly to the second packing 34 described in the first embodiment.

The ring-shaped portion 234b extends from the front end of the cylindrical portion 234a toward an outer-diameter direction of the second packing 234 and is slightly inclined toward a base-end side of the second packing 234.

The packing-side opening 234c is a vertically long ellipsoidal shape, and extends through the cylindrical portion 234a in a thickness direction of the cylindrical portion 234a. The length of the packing-side opening 234c in the vertical direction (the axial direction) of the base unit 230 is longer than the length of the packing-side opening 234c in a horizontal direction (a circumferential direction) of the base unit 230. An ellipsoidal rib 234d is provided on an inner circumferential surface of the cylindrical portion 234a, extends along an edge of the packing-side opening 234c, and protrudes toward an inner-diameter direction of the second packing 234.

The movable ring 242 includes an annular flange portion 242a in contact with the ring-shaped portion 234b of the second packing 234 and a movable cylinder 242b integrated with the flange portion 242a. The flange portion 242a has notch-like locking grooves 242c fitted to the base ends of the second locking protrusions 41c provided on the inner circumferential surface of the cup member 41. Therefore, the movable ring 242 rotates around the axis of the movable unit 240 integrally with the cup member 41. In the third embodiment, the movable ring 242 is made of a rigid plastic material (for example, polyacetal resin or polyamide resin) having elasticity.

As illustrated in FIG. 14B, the movable cylinder 242b has a plurality of movable-cylinder-side openings 242d (first openings). The movable cylinder-side openings 242d are small holes with different opening areas and are arranged at intervals in a circumferential direction of the movable ring 242.

In the third embodiment, nine movable-cylinder-side openings 242d are provided, the opening area of the movable-cylinder-side opening 242d(1) illustrated on the leftmost side in FIG. 14B is the smallest, the opening area of the movable-cylinder-side opening 242d(9) illustrated on the rightmost side in FIG. 14B is the largest, and the opening area of the movable-cylinder-side opening 242d becomes larger toward the rightmost side from the leftmost side.

The shapes and sizes of the movable-cylinder-side openings 242d are determined in such a manner that each of the movable-cylinder-side openings 242d can be positioned on the inner side of the packing-side opening 234c. The intervals at which the adjacent movable-cylinder-side openings 242d are arranged in the circumferential direction are determined in such a manner that only one of the movable-cylinder-side openings 242d can be positioned on the inner side of the packing-side opening 234c. However, the intervals at which the adjacent movable-cylinder-side openings 242d are arranged in the circumferential direction may be determined in such a manner that two or more of the movable-cylinder-side openings 242d can be positioned on the inner side of the packing-side opening 234c.

As illustrated in FIG. 14A, a guide plate 242e is provided on the inner circumferential surface of the movable cylinder 242b and present above a formation range of the movable-cylinder-side openings 242d. The guide plate 242e is attached to the inner circumferential surface of the movable cylinder 242b in such a manner that a gap is present between the guide plate 242e and the inner circumferential surface of the movable cylinder 242b due to attachment ribs 242f on an inner side of the movable cylinder 242b. The core member 10 in an inclined state can contact an inner circumferential surface of the guide plate 242e.

The guide plate 242e prevents inconvenience such as closing of the movable-cylinder-side openings 242d by the core member 10 in an inclined state. In other words, it can be said that the guide plate 242e is a guide member that secures air permeability of each of the movable-cylinder-side openings 242d.

A fitting protrusion 242g is formed on the movable cylinder 242b at a position 180 degrees opposite to the position of the guide plate 242e in the circumferential direction. The fitting protrusion 242g is present on a central portion of a plate string portion 242h in the circumferential direction and protrudes toward an outer side of the movable ring 242 in the same manner as the second embodiment.

The fitting protrusion 242g is fitted in any of the fitting slits 232d provided in the front end 232b of the second cylindrical member 232. The fitting protrusion 242g is fitted in any of the fitting slits 232d when any of the movable-cylinder-side openings 242d is positioned on the inner side of the packing-side opening 234c. When the fitting protrusion 242g fitted in any of the fitting slits 232d moves to an adjacent fitting slit 232d, rotational resistance of a movable unit 240 increases and decreases (click feeling).

This click feeling enables a user to recognize, based on tactile sensation, that the movable unit 240 has rotated and the amount of air has changed. Further, it is possible to reduce inconvenience such as the rotation of the movable unit 240 that is not intended by the user.

As illustrated in FIG. 16A, in the sperm collection device 1B according to the third embodiment, an inner circumferential surface of a base end of the movable unit 240 is arranged opposite to and overlaps an outer circumferential surface of a front end of the base unit 230. An airflow path AP for air flowing in and out of the container 20B and the adjustment mechanism AD2 that adjusts the flow rate of air in the flow air path AP are provided in an overlapping part in which the circumferential surfaces overlap each other.

The adjustment mechanism AD2 is constituted by a front-end portion (the front end 232b of the second cylindrical member 232 and the packing-side opening 234c) of the base unit 230 and a base-end portion (the movable ring 242 and the movable-cylinder-side openings 242d) of the movable unit 240.

A portion of the airflow path AP is constituted by a base-side index 32d (see FIG. 4) between the inner circumferential surface of the base end of the cup member 41 and the outer circumferential surface of the front end of the base unit 230. Air flows in and out of the container 20B through the airflow path AP and the adjustment mechanism AD2. Since the sperm collection device 1B according to the third embodiment includes the one packing-side opening 234c, the one base-side index 32d is provided. However, movable-side indices 41a (see FIG. 4) are arranged at intervals in a circumferential direction of the movable unit 240 in such a manner that the number of movable-side indices 41a corresponds to the number of movable-cylinder-side openings 242d.

Further, the adjustment mechanism AD2 adjusts, based on the area of one movable-cylinder-side opening 242d positioned on the inner side of the packing-side opening 234c, the flow rate (ease of the flow of air) of air flowing in and out of the container 20B.

Figure 17A:
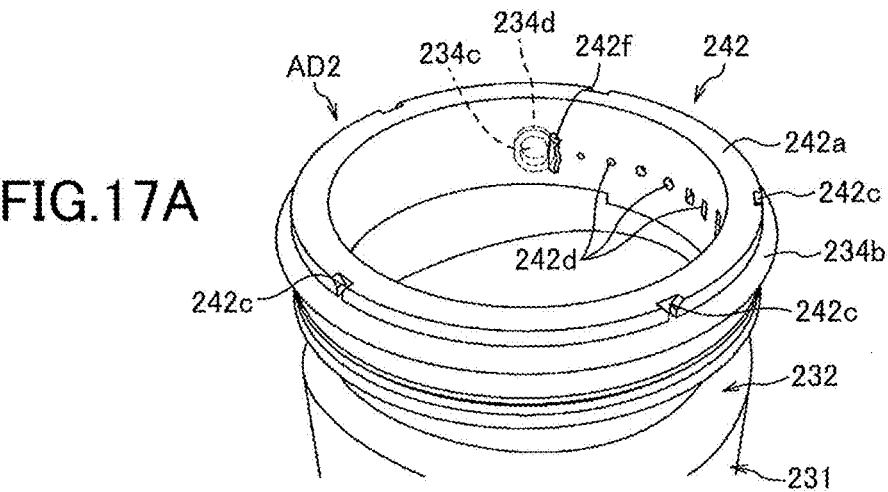
FIG. 17A is an explanatory diagram of a state in which any of movable-cylinder-side openings is not selected.
Figure 17B:
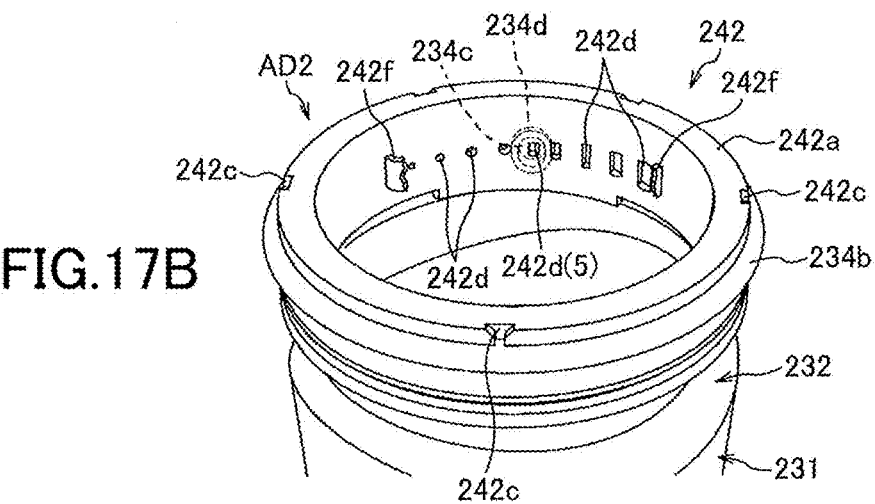
FIG. 17B is an explanatory diagram of a state in which one of the movable-cylinder-side openings is selected.
Figure 17C:
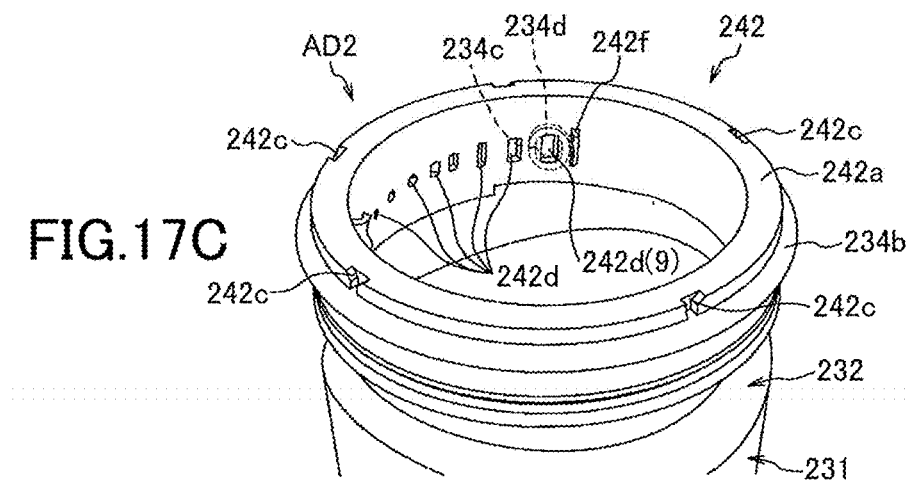
FIG. 17C is an explanatory diagram of a state in which another one of the movable-cylinder-side openings is selected.

FIG. 17A is an explanatory diagram of a state in which any of the movable-cylinder-side openings 242d is not selected, FIG. 17B is an explanatory diagram of a state in which one of the movable-cylinder-side openings 242d is selected, and FIG. 17C is an explanatory diagram of a state in which another one of the movable-cylinder-side openings 242d is selected.

In the example illustrated in FIG. 17A, any of the movable-cylinder-side openings 242d is not positioned on the inner side of the packing-side opening 234c. In this state, air flows only through a gap between the movable unit 240 and the base unit 230, a gap between the insertion space ES and the penis P, and the like, and stimulations given to the penis P are strongest.

In the example illustrated in FIG. 17B, the fifth movable-cylinder-side opening 242d(5) from the leftmost side is positioned on the inner side of the packing-side opening 234c, and air flows in and out of the container 20B with air resistance corresponding to the area of the fifth movable-cylinder-side opening 242d(5). In this state, stimulations given to the penis P are weaker than those in the example illustrated in FIG. 17A.

In the example illustrated in FIG. 17C, the movable-cylinder-side opening 242d(9) having the largest area and illustrated on the rightmost side is positioned on the inner side of the packing-side opening 234c, and stimulations given to the penis P are weaker than those in the example illustrated in FIG. 17B.

As described above, in the sperm collection device 1B according to the third embodiment, the flow rate of air flowing in and out of the container 20B is adjusted based on a rotational angle of the movable unit 240 (the cup member 41) with respect to the base unit 230. Therefore, it is possible to adjust the strength of stimulations to be given to the penis P based on the rotational angle.

Modifications

In each of the foregoing embodiments, the inner circumferential surface of the base end of the movable unit 40, 140, or 240 and the outer circumferential surface of the front end of the base unit 30, 130, or 230 are arranged opposite to each other and the second packing 34, 134, or 234 with the packing-side opening 34c, 134c, or 234c is interposed between the two circumferential surfaces. However, each of the embodiments is not limited to this configuration.

For example, in each of the foregoing embodiments, the adjustment mechanism AD, AD1, or AD2 is provided at an intermediate position in the container 20, 20A, or 20B in the axial direction of the container 20, 20A, or 20B, but may be provided at the front end (a front-end-side surface or a front-end surface) of the container 20, 20A, or 20B in the axial direction.

Further, the front end of the base unit 30 or the like may have a double structure with an outer circumferential wall and an inner circumferential wall, the base end of the movable unit 40 or the like may be fitted in a groove between the outer circumferential wall and the inner circumferential wall, and the second packing 34 or the like may be interposed between the base end of the movable unit and the inner circumferential wall of the base unit. In this configuration, a base-end-side surface of the movable unit 40 or the like and the inner circumferential wall of the base unit 30 or the like are arranged opposite to each other via the second packing 34 or the like. Therefore, operational effects identical to those obtained in the above embodiments can be obtained by forming an opening in each of the base-end-side surface of the movable unit 40 or the like, the inner circumferential wall of the base unit 30 or the like, and the second packing 34 or the like.

In each of the foregoing embodiments, the insertion space ES of the core member 10 and the internal space IS of the container 20 or the like do not communicate with each other. However, as illustrated in FIGS. 1A and 1B and the like, a valve 11f that enables the internal space IS of the container 20 and the insertion space ES of the core member 10 to communicate with each other may be provided near a front-end portion of the core member 10.

In this case, the valve 11f is provided in a portion (for example, the front-end portion) of the core member 10 and is a linear notch extending through the cylindrical portion 11c in a thickness direction of the cylindrical portion 11c. The valve 11f is continuously closed due to elasticity of an elastic material. However, when the pressure of air in the insertion space ES is equal to or higher than a predetermined level, the valve 11f is opened to cause the insertion space ES to communicate with the internal space IS and allows air to be discharged.

In this manner, the valve 11f allows air to be discharged from the insertion space ES to the internal space IS of the container 20 and limits the flow of air from the internal space IS of the container 20 to the insertion space ES.

Regarding the adjustment mechanisms AD, AD1, and AD2, in each of the foregoing embodiments, the curved-portion-side opening 42e or the movable-cylinder-side opening 142g or 242g is provided in the movable ring 42, 142, or 242, while the packing-side openings 34c, or the packing-side openings 134c and the base-side openings 132c, or the packing-side openings 234c are provided in the base unit 30, 130, or 230. However, each of the foregoing embodiments is not limited to this configuration.

It suffices as long as each of the adjustment mechanisms AD, AD1, and AD2 can adjust the flow rate of air flowing in and out of the container 20, 20A, or 20B based on a rotational angle of the movable unit 40, 140, or 240 with respect to the base unit 30, 130, or 230.

Figure 18:
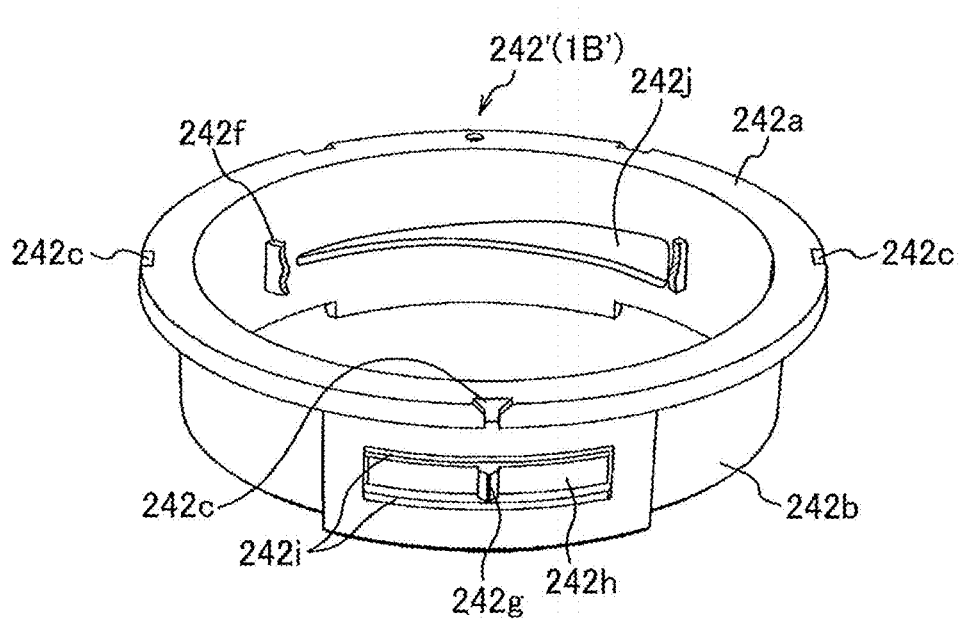
FIG. 18 is an explanatory diagram of a movable ring included in a sperm collection device according to a modification of the third embodiment.

FIG. 18 is an explanatory diagram of a movable ring 242' included in a sperm collection device 1B' according to a modification of the third embodiment, FIG. 19A is an explanatory diagram of a state in which a movable-cylinder-side opening 242j does not overlap the packing-side opening 234c, FIG. 19B is an explanatory diagram of a state in which the flow rate of air is adjusted to an intermediate level, and FIG. 19C is an explanatory diagram of a state in which the flow rate of air is adjusted to the maximum level.

As illustrated in FIG. 18, the sperm collection device 1B' includes the movable ring 242'. The movable ring 242' has the movable-cylinder-side opening 242j (a first opening). The movable-cylinder-side opening 242j has an elongated shape in a circumferential direction of the movable ring 242' and has an opening height (the length in an axial direction of the sperm collection device 1B') varying depending on a position in the circumferential direction. The movable-cylinder-side opening 242j exemplified in FIG. 18 has a substantially-triangular and elongated shape in the circumferential direction. Specifically, the opening height of the movable-cylinder-side opening 242j at one end (the left end) of the opening 242j in the circumferential direction is smallest, while the opening height of the movable-cylinder-side opening 242j at the other end (the right end) of the opening 242j in the circumferential direction is largest. The opening height of the movable-cylinder-side opening 242j gradually (continuously) increases toward the other end from the one end in the circumferential direction. That is, the opening height of the movable-cylinder-side opening 242j gradually (continuously) decreases toward the one end from the other end in the circumferential direction. The shape of the movable-cylinder-side opening 242j is not limited to the example of FIG. 18.

As illustrated in FIGS. 19A to 19C, the packing-side opening 234c (the second opening) provided in the second packing 234 has a length in the circumferential direction of the second packing 234 smaller than the length of the movable-cylinder-side opening 242j in the circumferential direction of the movable ring 242' and has an opening height equal to or larger than the opening height (the maximum length in the axial direction) of the movable-cylinder-side opening 242j at the other end of the movable-cylinder-side opening 242j in the circumferential direction.

In the sperm collection device 1B' according to the modification of the third embodiment, configurations other than those described above are identical to those of the sperm collection device 1B according to the third embodiment and thus explanations thereof are omitted.

In an adjustment mechanism AD2' illustrated in FIGS. 19A to 19C, the area of the movable-cylinder-side opening 242j (the first opening) positioned on the inner side of the packing-side opening 234c (the second opening) changes based on a rotational angle of the movable unit 130 with respect to the base unit 230. The adjustment mechanism AD2' adjusts, based on the area of the movable-cylinder-side opening 242j positioned on the inner side of the packing-side opening 234c, the flow rate (ease of the flow of air) of air flowing in and out of the container.

In the example illustrated in FIG. 19A, the movable-cylinder-side opening 242j is not positioned on the inner side of the packing-side opening 234c. In this state, air flows only through a gap between the movable unit 240 and the base unit 230, a gap between the insertion space ES and the penis P, and the like, and stimulations given to the penis P are strongest.

In the example illustrated in FIG. 19B, a central part of the movable-cylinder-side opening 242j in the circumferential direction is positioned on the inner side of the packing-side opening 234c, and thus air flows in and out of the container with air resistance corresponding to the area of the overlapping central part of the opening 242j with the packing-side opening 234c. In this state, stimulations given to the penis P are weaker than those in the example illustrated in FIG. 19A.

In the example illustrated in FIG. 19C, the right end of the movable-cylinder-side opening 242j in the circumferential direction is positioned on the inner side of the packing-side opening 234c, and stimulations given to the penis P are weaker than those in the example illustrated in FIG. 19B.

The configuration of the core member 10 is not limited to that illustrated in FIG. 3. For example, the number of the ring members 12 may be one or two, or the ring members 12 may be omitted.

The outer shape of the cup member 41 is not limited as long as the cup member 41 is rotatable around the axis with respect to the base unit 30. For example, the cup member 31 may have an outer rectangular parallelepiped shape.

Regarding the airflow path AP, the foregoing embodiments exemplify the configuration in which the base-side indices 32d are constituted by grooves and used as the airflow path AP. However, the embodiments are not limited to this configuration. A groove may be formed on an inner surface of the cup member 41 or a gap may be present between the inner circumferential surface of the base end of the cup member 41 and the outer circumferential surface of the front end of the second cylindrical member 32.

Summary of Actions and Effects of Aspects of the Present Invention

First Aspect

Each of the sperm collection devices 1, 1A, and 1B according to the present aspect includes the core member 10 made of an elastic material, with the insertion hole 11a for the penis P and the insertion space ES in which the penis P inserted in the insertion hole 11a moves inwardly and outwardly, and the container 20, 20A, or 20B in which the core member 10 is accommodated in the internal space IS. The container 20 or the like includes the cylindrical base unit 30, 130, or 230 having the front end open in the axial direction of the base unit and the base end (one end) open in the axial direction and attached to the insertion-hole-side end portion of the core member 10, and the cylindrical (cup-shaped) movable unit 40, 140, or 240 having the base end open in the axial direction of the movable unit and the front end being closed, and attached rotatably around the axis with respect to the front end of the base unit 30 or the like. The base end of the movable unit 40 or the like overlaps the front end (the other end) of the base unit 30 or the like. The container 20 or the like includes the airflow path AP in the overlapping part in which the base end of the movable unit 40 or the like overlaps the front end of the base unit 30 or the like. In the overlapping part, the adjustment mechanism AD, AD1, or AD2 that adjusts the flow rate of air flowing in and out of the container 20 or the like based on a rotational angle of the movable unit 40 or the like with respect to the base unit 30 or the like is provided.

In each of the sperm collection devices 1 and the like according to the present aspect, the adjustment mechanism AD or the like adjusts the flow rate of air based on a rotational angle of the movable unit 40 or the like with respect to the base unit 30 or the like to adjust stimulations to be given to the top end portion TP of the penis P. Further, since the airflow path AP is provided in the overlapping part in which the base end of the movable unit 40 or the like and the front end of the base unit 30 or the like are arranged opposite to each other, the user hardly closes the airflow path AP with his fingers when the sperm collection device 1 or the like is used, and it is possible to prevent a change in stimulations that is not intended by the user.

Second Aspect

In each of the sperm collection devices 1 according to the present aspect, the core member 10 has the valve 11f that is opened when the top end portion PT of the penis P moves toward the inner side of the insertion space ES, and is closed when the top end portion PT moves toward the insertion hole 11a from the inner side of the insertion space ES.

In each of the sperm collection devices 1 and the like according to the present aspect, the core member 10 includes the valve 11f, and when the top end portion PT of the penis P moves toward the insertion hole 11a from the inner side of the insertion space ES, the contact of the top end portion PT of the penis P with the inner circumferential surface of the core member 10 becomes stronger and it is possible to give stronger stimulations to the top end portion PT of the penis P.

Third Aspect

In each of the sperm collection devices 1 and the like according to the present aspect, the movable unit 40 or the like includes the cylindrical cup member 41 having the base end being open and the front end being closed, and the movable member (the movable ring 42, 142, or 242) adjacent to the inner circumferential surface of the front end side portion of the base unit 30 or the like via the second packing 34, 134, or 234, rotatable integrally with the cup member 41, and having the first opening (the curved-portion-side opening 42e or the movable-cylinder-side opening 142g or 242d). The base unit 30 or the like includes at least one second opening (the packing-side openings 34c or 134c or the packing-side opening 234c) formed at a position where the second opening communicates with the airflow path AP at the front end of the base unit 30 or the like, the adjustment mechanism AD, AD1, or AD2 can change the opening area of an overlapping part in which the first opening overlaps the second opening based on a rotational angle of the movable unit 40 or the like with respect to the base unit 30 or the like.

In the sperm collection device 1 according to the present aspect, the opening area of an overlapping part in which the first opening overlaps the second opening can be changed based on a rotational angle of the movable unit 40 with respect to the base unit 30, and thus the flow rate of air can be adjusted with high accuracy based on the opening area of the overlapping part.

Fourth Aspect

In the sperm collection device 1 according to the present aspect, the first opening (the curved-portion-side opening 42e) has an elongated shape in the circumferential direction of the movable unit 40, the plurality of second openings (the packing-side openings 34c) are arranged at intervals in the circumferential direction of the base unit 30, and the adjustment mechanism AD can change the number of second openings positioned on the inner side of the first opening based on a rotational angle of the movable unit 40 with respect to the base unit 30.

In the sperm collection device 1 according to the present aspect, it is possible to adjust the flow rate of air with high accuracy based on the number of second openings positioned on the inner side of the first opening.

Fifth Aspect

In the sperm collection device 1A according to the present aspect, the plurality of second openings (the packing-side openings 134c) are arranged at intervals in the circumferential direction of the base unit 130, the opening areas of the second openings are different, the first opening (the movable-cylinder-side opening 142g) has a shape enabling one of the second openings to be positioned on the inner side of the first opening, and the adjustment mechanism AD1 selects one of the second openings based on a rotational angle of the movable unit 140 with respect to the base unit 130 and causes the one second opening to be positioned on the inner side of the first opening.

In the sperm collection device 1A according to the present aspect, it is possible to adjust the flow rate of air with high accuracy based on the opening area of a second opening positioned on the inner side of the first opening.

Sixth Aspect

In the sperm collection device 1B according to the present aspect, the plurality of first openings (the movable-cylinder-side openings 242d) are arranged at intervals in the circumferential direction of the movable unit 240, the opening areas of the first openings are different, the second opening (the packing-side opening 234c) has a shape enabling one of the first openings to be positioned on an inner side of the second opening, and the adjustment mechanism AD2 selects one of the first openings based on a rotational angle of the movable unit 240 with respect to the base unit 230 and causes the one first opening to be positioned on the inner side of the second opening.

In the sperm collection device 1B according to the present aspect, it is possible to adjust the flow rate of air with high accuracy based on the opening area of a first opening positioned on the inner side of the second opening.

Seventh Aspect

In the sperm collection device 1B' according to the present aspect, the first opening (the movable-cylinder-side opening 242j) has an elongated shape in the circumferential direction of the movable unit 240 and has a length (an opening height) in the axial direction of the movable unit 240 that varies depending on a position in the circumferential direction, the second opening (the packing-side opening 234c) has a length in the circumferential direction of the base unit 230 smaller than the length of the first opening in the circumferential direction of the movable unit 240, the length of the second opening in the axial direction of the base unit 230 is equal to or larger than the maximum length of the first opening in the axial direction of the movable unit 240, and the adjustment mechanism AD2' can change the area of the first opening positioned on the inner side of the second opening based on a rotational angle of the movable unit 240 with respect to the base unit 230.

In the sperm collection device 1B' according to the present aspect, it is possible to adjust the flow rate of air with high accuracy based on the opening area of the first opening positioned on the inner side of the second opening.

What is claimed is:

1. A sperm collection device, the sperm collection device comprising:
   a core member that is made of an elastic material and has an insertion hole for a penis and an insertion space in which the penis inserted in the insertion hole relatively moves inwardly and outwardly; and
   a container having an internal space in which the core member is accommodated, wherein
   the container includes
   a cylindrical base unit that has one end open in an axial direction of the base unit and attached to an insertion-hole-side end of the core member and an opposite end open in the axial direction, and
   a cylindrical movable unit that has one end open in an axial direction of the movable unit and an opposite end being closed and is attached rotatably around an axis of the movable unit with respect to the opposite end of the base unit, the one end of the movable unit overlaps the opposite end of the base unit, and an airflow path is provided in an overlapping part in which the one end of the movable unit overlaps the opposite end of the base unit, and an adjustment mechanism that adjusts, based on a rotational angle of the movable unit with respect to the base unit, a flow rate of air flowing in and out of the container is provided in the overlapping part.

2. The sperm collection device according to claim 1, wherein the core member includes a valve that is opened when the penis moves toward an inner side of the insertion space, and is closed when the penis moves toward the insertion hole from the inner side.

3. The sperm collection device according to claim 1, wherein the movable unit includes a cylindrical cup member having one end being open and an opposite end being closed and a movable member adjacent to an inner circumferential surface of the opposite end of the base unit in the axial direction of the base unit via a packing, rotatable integrally with the cup member, and having a first opening formed therein, the base unit has a second opening formed at a position where the second opening communicates with the airflow path at the opposite end in the axial direction of the base unit, and the adjustment mechanism is configured to be able to change, based on a rotational angle of the movable unit with respect to the base unit, an opening area of an overlapping part in which the first opening overlaps the second opening.

4. The sperm collection device according to claim 3, wherein the first opening has an elongated shape in a circumferential direction of the movable unit, the second opening is provided in plural and the plurality of second openings are arranged at intervals in a circumferential direction of the base unit, and the adjustment mechanism is configured to be able to change a number of second openings positioned on an inner side of the first opening based on a rotational angle of the movable unit with respect to the base unit.

5. The sperm collection device according to claim 3, wherein the second opening is provided in plural and the plurality of second openings are arranged at intervals in a circumferential direction of the base unit and have mutually different opening areas, the first opening has a shape enabling one of the second openings to be positioned on an inner side of the first opening, and the adjustment mechanism causes one of the second openings to be positioned on the inner side of the first opening based on a rotational angle of the movable unit with respect to the base unit.

6. The sperm collection device according to claim 3, wherein the first opening is provided in plural and the plurality of first openings are arranged at intervals in a circumferential direction of the movable unit and have mutually different opening areas, the second opening has a shape enabling one of the first openings to be positioned on an inner side of the second opening, and the adjustment mechanism causes one of the first openings to be positioned on the inner side of the second opening based on a rotational angle of the movable unit with respect to the base unit.

7. The sperm collection device according to claim 3, wherein the first opening has an elongated shape in a circumferential direction of the movable unit and has a length in the axial direction of the movable unit that varies depending on a position in the circumferential direction, the second opening has a length in a circumferential direction of the base unit shorter than a length of the first opening in the circumferential direction of the movable unit, and a length of the second opening in the axial direction of the base unit is equal to or larger than a maximum length of the first opening in the axial direction of the movable unit, and the adjustment mechanism is configured to be able to change the opening area of the first opening positioned on an inner side of the second opening based on a rotational angle of the movable unit with respect to the base unit.

* * * * *